(12) United States Patent
Ozcan

(10) Patent No.: US 9,202,835 B2
(45) Date of Patent: Dec. 1, 2015

(54) MICROSCOPY METHOD AND SYSTEM INCORPORATING NANOFEATURES

(75) Inventor: Aydogan Ozcan, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 68 days.

(21) Appl. No.: 13/824,793

(22) PCT Filed: Oct. 14, 2011

(86) PCT No.: PCT/US2011/056439
§ 371 (c)(1),
(2), (4) Date: Mar. 18, 2013

(87) PCT Pub. No.: WO2012/054351
PCT Pub. Date: Apr. 26, 2012

(65) Prior Publication Data
US 2013/0193544 A1    Aug. 1, 2013

Related U.S. Application Data

(60) Provisional application No. 61/394,289, filed on Oct. 18, 2010.

(51) Int. Cl.
*H01L 27/146* (2006.01)
*B82Y 15/00* (2011.01)
*G01B 21/00* (2006.01)
(Continued)

(52) U.S. Cl.
CPC ........... *H01L 27/14625* (2013.01); *B82Y 15/00* (2013.01); *G01B 21/00* (2013.01); *G01N 21/253* (2013.01); *G01N 21/41* (2013.01)

(58) Field of Classification Search
CPC .. B82Y 15/00; H01L 27/14625; G01N 21/41; G01N 21/253; G01B 21/00
See application file for complete search history.

(56) References Cited

U.S. PATENT DOCUMENTS 7,456,383 B2    11/2008  Kim et al.
2007/0207061 A1*  9/2007  Yang et al. ................ 422/82.05
(Continued)

OTHER PUBLICATIONS

Elkhatib, Tamer A. et al., High Resolution Imaging through Integrated Nanoholes Image Sensor, Biomedical Circuits and Systems Conference, Nov. 20, 2008, pp. 245-248.
(Continued)

*Primary Examiner* — Marvin Payen
*Assistant Examiner* — Victor Barzykin
(74) *Attorney, Agent, or Firm* — Vista IP Law Group LLP

(57) ABSTRACT

A lensfree imaging and sensing device includes an image sensor comprising an array of pixels and a substantially optically transparent layer disposed above the image sensor. Nano-sized features that support surface plasmon waves are populated on the substantially optically transparent layer separating the image sensor from the nano-sized features. The nano-sized features may include apertures through a substantially optically opaque layer (e.g., metal layer) or they may include antennas. An illumination source is provided that is configured to illuminate a sample. At least one processor is operatively coupled to the image sensor. Changes to the detected transmission pattern at the image sensor are used to sense conditions at or near the surface containing the nano-sized features. Conditions may include binding events or other changes to the index of refraction occurring near the surface of the device.

13 Claims, 13 Drawing Sheets

(51) Int. Cl.
　　　G01N 21/25　　(2006.01)
　　　G01N 21/41　　(2006.01)

(56) References Cited

U.S. PATENT DOCUMENTS

| | | | |
|---|---|---|---|
| 2007/0258096 A1* | 11/2007 | Cui et al. | 356/521 |
| 2008/0278728 A1* | 11/2008 | Tetz et al. | 356/445 |
| 2010/0108882 A1* | 5/2010 | Zewail | 250/307 |
| 2010/0140460 A1 | 6/2010 | Rigneault et al. | |

OTHER PUBLICATIONS

Liu, Zhengtong et al., Plasmonic nanoantenna arrays for the visible, Metamaterials vol. 2, Mar. 2008, pp. 45-51.

PCT International Search Report for PCT/US2011/056439, Applicant: The Regents of the University of California, Form PCT/ISA/210 and 220, dated May 8, 2012 (5pages).

PCT Written Opinion of the International Search Authority for PCT/US2011/056439, Applicant: The Regents of the University of California, Form PCT/ISA/237, dated May 8, 2012 (6pages).

Abajo "Light transmission through a single cylindrical hole in a metallic film" Optics Express dated Dec. 16, 2002, vol. 10, No. 25 (10 pages).

Baida, et al. "Subwavelength metallic coaxial waveguides in the optical range: Role of the plasmonic modes" Physical Review B 74, 205419, Nov. 16, 2006 (7 pages).

Caglayan, et al. "Beaming of electromagnetic waves emitted through a subwavelength annular aperture" Optical Society of America dated Mar. 2006, vol. 23, No. 3 (4 pages).

Degiron, et al. "Optical transmission properties of a single subwavelength aperture in a real metal" Optics Communications dated May 2004 (6 pages).

Garcia-Vidal, et al. "Transmission of Light through a Single Rectangular Hole" Physical Review PRL 95, 103901, published 2005 (4 pages).

Garcia-Vidal, et al. "Transmission of light through a single rectangular hole in a real metal" Physical Review B 74, 153411, published Oct. 18, 2006 (4 pages).

Jin, et al. "Obtaining super resolution light spot using surface plasmon assisted sharp ridge nanoaperture" Applied Physics Letters 86, 111106, Mar. 8, 2005 (3 pages).

Lockyear, et al. "Microwave Transmission through a Single Subwavelength Annular Aperture in a Metal Plate" Physical Review Letters published May 17, 2005, vol. 94 (4 pages).

Matteo, et al. "Spectral analysis of strongly enhanced visible light transmission through single C-shaped nanoapertures" Applied Physics Letters dated Jul. 26, 2004, vol. 85, No. 4 (4 pages).

Moreau, et al. "Light transmission by subwavelength square coaxial aperture arrays in metallic films" Optics Express dated May 19, 2003, vol. 11, No. 10 (6 pages).

Novotny, et al. "Principles of Nano-Optics" published in 2006 by Cambridge University Press, pp. 378-418.

Oh et al. "On-chip differential interference contrast microscopy using lensless digital holography" Optics Express dated Mar. 1, 2010, vol. 18, No. 5 (10 pages).

Popov, et al. "Field enhancement in single subwavelength apertures" Optical Society of America dated Sep. 2006, vol. 23, No. 9 (7 pages).

Roberts "Electromagnetic theory of diffraction by a circular aperture in a thick, perfectly conducting screen" optical Society of America dated Oct. 1987, vol. 4, No. 10 (14 pages).

Shi "Design of a C Aperture to achieve X/10 resolution and resonant transmission" Optical Society of America dated Jul. 2004, vol. 21, No. 7 (13 pages).

Sun, et al. "Low-loss subwavelength metal C-aperture waveguide" Optics Letters dated Dec. 15, 2006, vol. 31, No. 24 (3 pages).

Tseng et al. "Lensfree microscopy on a cellphone" Lab on a Chip 10,1787, published May 6, 2010 (7 pages).

Zakharian, et al. "Transmission of light through small elliptical apertures" Optics Express dated Jun. 14, 2004, vol. 12, No. 12 (18 pages).

Hardie et al., Joint MAP Registration and High-Resolution Image Estimation Using a Sequence of Undersampled Images, IEEE, vol. 6 No. 12, Dec. 1997.

Ozcan et al., Ultra wide-filed lens-free monitoring of cells on-chip, Lab on Chip 8, 89-106, Nov. 1, 2007.

Ozcan et al., Lens-free On-Chip Cytometry for wireless Health Diagnosis, IEEE LEOS Newsletter, Oct. 2008.

Seo et al., Lensfree On-chip Cytometry Using Tunable Monochromatic Illumination and Digital Noise Reduction, Multi-color LUCAS, Sep. 2008.

Seo et al., Lensfree holographic imaging for on-chip cytometry and diagnostics, Lab on a Chip, 9, 777-787, Dec. 5, 2008.

Su et al., Towards Wireless Health: Lensless On-Chip Cytometry, Biophotonics, Dec. 2008.

Su et al., High-Throughput Lensfree Imaging and Characterization of Heterogeneous Cell Solution on a Chip, Biotechnology and Bioengineering, Sep. 8, 2008.

Isikman et al., Lensfree Cell Holography on a Chip: From Holographic Cell Signatures to Microscopic Reconstruction, LEOS Annual Meeting Conf. Proceedings, Oct. 2009.

Mudanyali et al., Lensless On-chip Imaging of Cells Provides a New Tool for High-throughput Cell-Biology and Medical Diagostics, Journal of Visualized Experiments, Dec. 14, 2009.

Bishara et al., Lensfree on-chip microscopy over a wide field-of-view using pixel super-resolution, Optics Express, vol. 18 No. 11, May 24, 2010.

Coskun et al., Wide field-of-view lens-free fluorescent imaging on a chip, Lab Chip, 10(7), 824-827, Apr. 7, 2010.

Coskun et al., Lensless wide-field fluorescent imaging on a chip using compressive decoding of sparse objects, Optics Express, vol. 18 No. 10, May 5, 2010.

Khademhosseinieh et al., Lensfree color imaging on a nanostructured chip using compressive decoding, Applied Physics Letters, 97, 211112-1, Nov. 24, 2010.

Khademhosseinieh et al., Lensfree on-chip imaging using nanostructured surfaces, Applied Physics Letters, 96, 171106, Apr. 30, 2010.

Mudanyali et al., Compact, light-weight and cost-effective microscope based on lensless incoherent holography for telemedicine applications, Lab Chip, 10, 1417-1428, Apr. 19, 2010.

Ozcan, Smart technology for global access to healthcare, SPIE, Mar. 16, 2010.

Ozcan et al., Lensfree on-chip holography facilitates novel microscopy applications, SPIE, May 19, 2010.

PCT International Preliminary Report on Patentability (Chapter I of the Patent Cooperation Treaty) for PCT/US2011/056439, Applicant: The Regents of the University of California, Form PCT/IB/326 and 373, dated Apr. 23, 2013 (7pages).

* cited by examiner

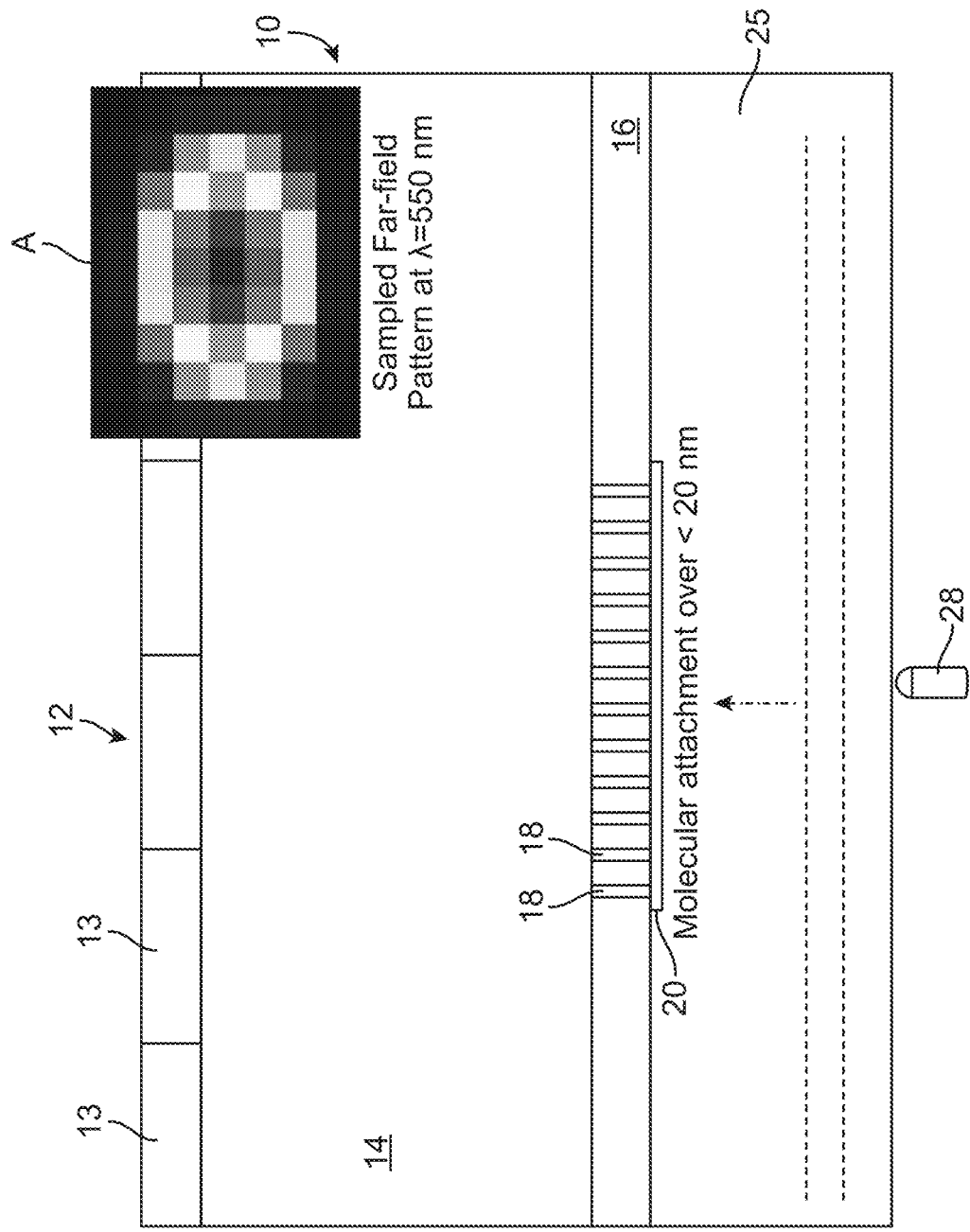

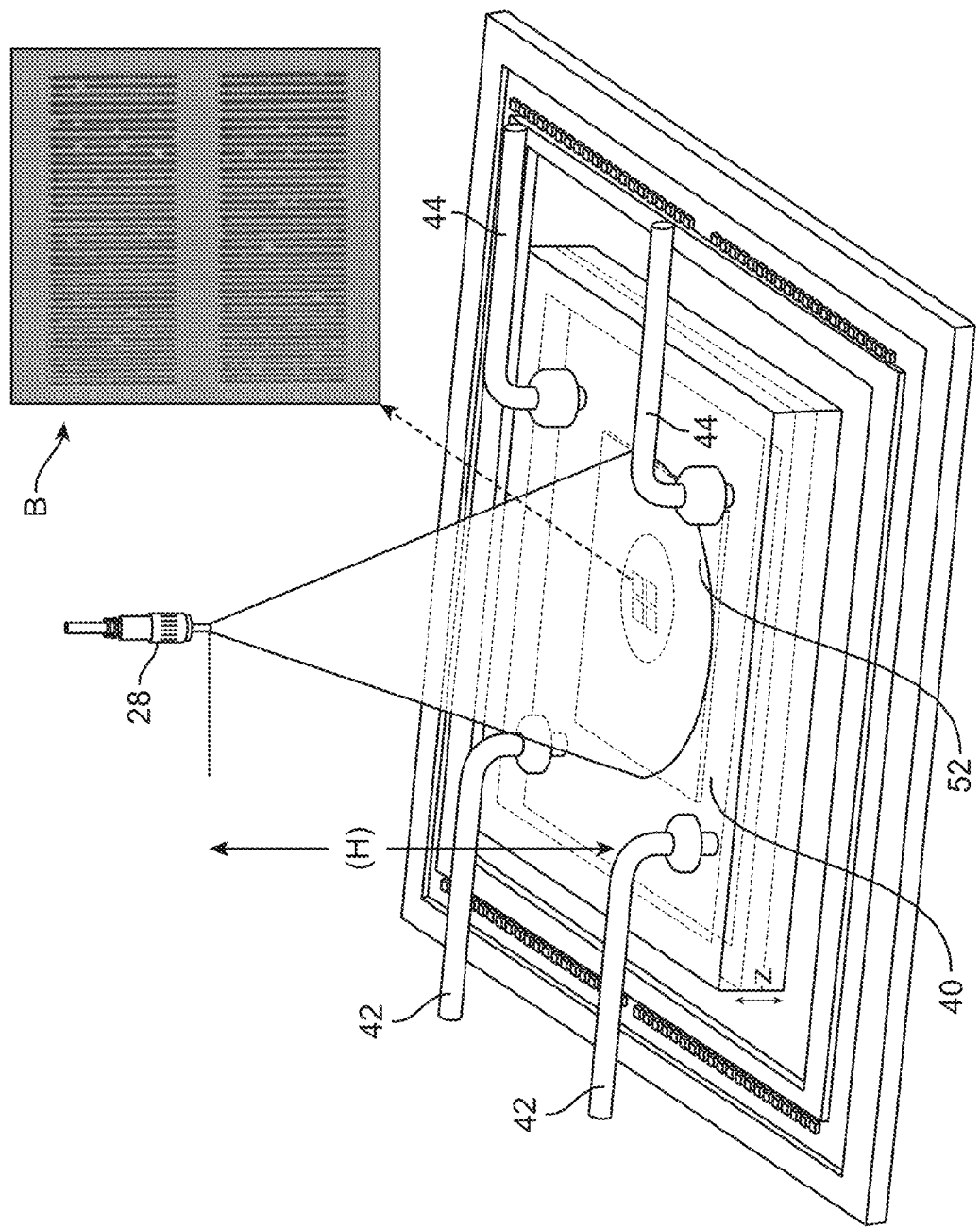

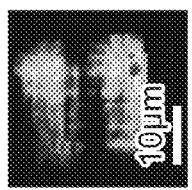
FIG. 6A  Z = 1100μm
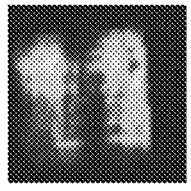
FIG. 6D  Z = 1μm
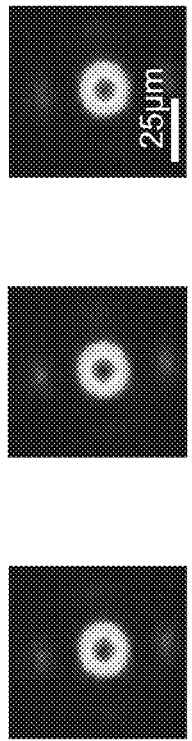
FIG. 6B  FIG. 6C  FIG. 6E  FIG. 6F
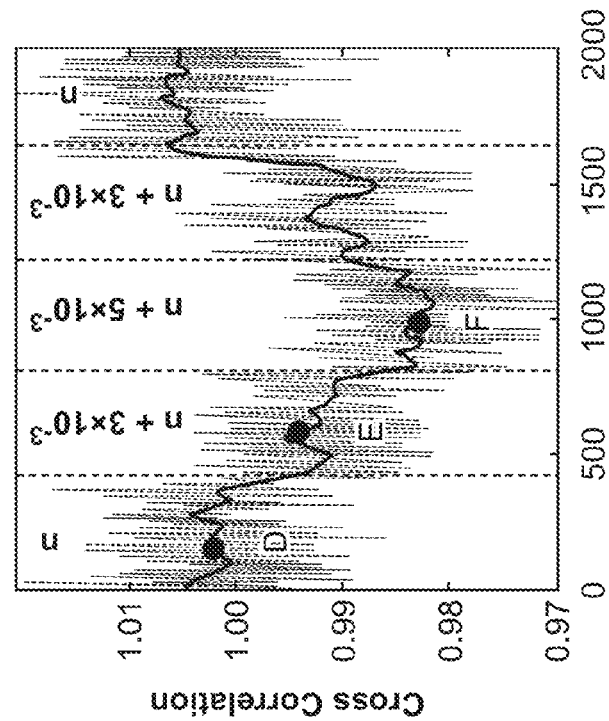
FIG. 7A
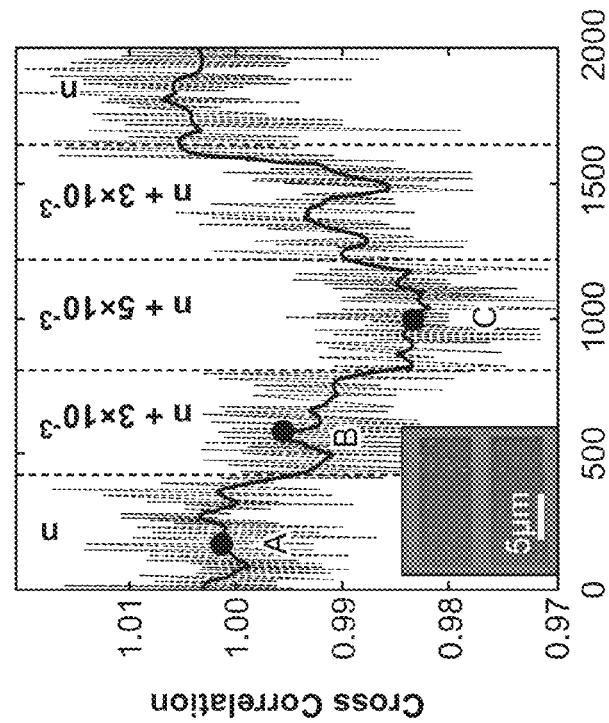
FIG. 7B

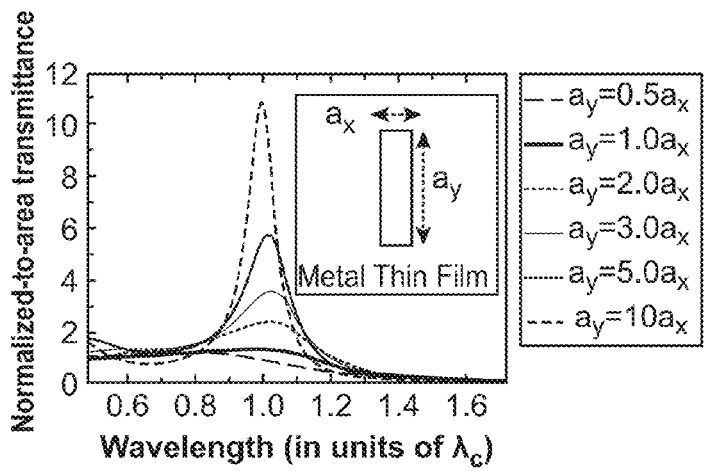

FIG. 10

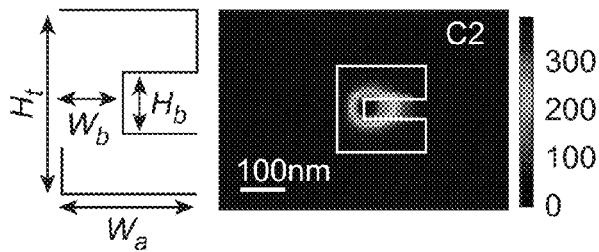

FIG. 11

| $\lambda_{36}$ | $\lambda_{15}^*$ | $\lambda_6$ | $\lambda_{31}^*$ | $\lambda_{50}$ | $\lambda_{38}^*$ | $\lambda_{41}$ | $\lambda_2^*$ | $\lambda_{16}$ | $\lambda_{37}^*$ |
|---|---|---|---|---|---|---|---|---|---|
| $\lambda_{32}^*$ | $\lambda_{12}$ | $\lambda_{18}^*$ | $\lambda_{21}$ | $\lambda_3^*$ | $\lambda_{46}$ | $\lambda_{23}^*$ | $\lambda_{26}$ | $\lambda_{29}^*$ | $\lambda_{49}$ |
| $\lambda_{25}$ | $\lambda_{44}^*$ | $\lambda_9$ | $\lambda_{25}^*$ | $\lambda_{34}$ | $\lambda_{17}^*$ | $\lambda_{11}$ | $\lambda_{34}^*$ | $\lambda_8$ | $\lambda_{12}^*$ |
| $\lambda_{39}^*$ | $\lambda_1$ | $\lambda_{48}^*$ | $\lambda_{29}$ | $\lambda_{41}^*$ | $\lambda_{38}$ | $\lambda_{49}^*$ | $\lambda_2$ | $\lambda_{16}^*$ | $\lambda_{23}$ |
| $\lambda_{20}$ | $\lambda_{14}^*$ | $\lambda_5$ | $\lambda_{21}^*$ | $\lambda_{45}$ | $\lambda_6^*$ | $\lambda_{27}$ | $\lambda_{30}^*$ | $\lambda_{39}$ | $\lambda_{27}$ |
| $\lambda_9^*$ | $\lambda_{33}$ | $\lambda_{24}^*$ | $\lambda_{10}$ | $\lambda_{33}^*$ | $\lambda_{24}$ | $\lambda_{13}^*$ | $\lambda_{42}$ | $\lambda_5^*$ | $\lambda_{48}$ |
| $\lambda_{30}$ | $\lambda_{42}^*$ | $\lambda_{37}$ | $\lambda_1^*$ | $\lambda_{40}$ | $\lambda_{50}^*$ | $\lambda_{19}$ | $\lambda_{10}^*$ | $\lambda_{22}$ | $\lambda_{45}^*$ |
| $\lambda_{46}^*$ | $\lambda_{13}$ | $\lambda_4^*$ | $\lambda_{47}$ | $\lambda_{43}^*$ | $\lambda_4$ | $\lambda_{28}^*$ | $\lambda_{31}$ | $\lambda_{35}^*$ | $\lambda_{18}$ |
| $\lambda_7$ | $\lambda_{20}^*$ | $\lambda_{17}$ | $\lambda_8^*$ | $\lambda_{32}$ | $\lambda_{22}^*$ | $\lambda_{15}$ | $\lambda_{40}^*$ | $\lambda_3$ | $\lambda_7^*$ |
| $\lambda_{26}^*$ | $\lambda_{43}$ | $\lambda_{36}^*$ | $\lambda_{28}$ | $\lambda_{11}^*$ | $\lambda_{35}$ | $\lambda_{19}^*$ | $\lambda_{44}$ | $\lambda_{47}^*$ | $\lambda_{14}$ |

FIG. 12

MICROSCOPY METHOD AND SYSTEM INCORPORATING NANOFEATURES

RELATED APPLICATION

This Application is a U.S. National Stage filing under 35 U.S.C. §371 of International Application No. PCT/US2011/056439, filed Oct. 18, 2010, which claims priority to U.S. Provisional Patent Application No. 61/394,289 filed on Oct. 18, 2010. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

FIELD OF THE INVENTION

The field of the invention generally relates to imaging systems and methods. More particularly, the field of the invention relates to imaging devices and methods for use in optical sensing and/or imaging applications.

BACKGROUND

Lensfree imaging has been recently gaining more emphasis to create modalities that can potentially eliminate bulky optical components to perform microscopy on a chip. Such on-chip microscope designs would especially benefit microfluidic systems to create powerful capabilities especially for medical diagnostics and cytometry applications. Being lightweight and compact, lensfree imaging can also potentially create an important alternative to conventional lens-based microscopy especially for telemedicine applications.

Metallic apertures support surface plasmon waves that are localized to the near-field of the aperture structure. Physical properties of these plasmonic waves, by their nature, are rather sensitive to the local refractive index of the medium surrounding the aperture region. As the size of the metallic aperture goes sub-wavelength, direct transmission of light through the aperture becomes extremely inefficient and the transmission behavior of these apertures starts to be dominated by plasmonic effects, exhibiting strong sensitivity to the refractive index of the surrounding medium as well as to the wavelength, polarization, and the angle of the illumination light. Surface plasmon resonance using metal films has been used, for example, gas detection and biosensing applications. While metallic films and apertures have been used in some sensing applications, these have not been integrated into a lensfree system that avoids the need for lenses, mechanical scanning or other bulky optical/mechanical components.

SUMMARY

In one embodiment, a lensfree imaging and sensing device includes an image sensor comprising an array of pixels and a substantially optically transparent layer disposed above the image sensor. A substantially optically opaque layer is disposed above the substantially optically transparent layer, the substantially optically opaque layer comprising a plurality of apertures extending through the substantially optically opaque layer and configured to receive a sample thereon. The device includes an illumination source configured to illuminate the sample and at least one processor operatively coupled to the image sensor.

In another embodiment, a lensfree imaging and sensing device includes a image sensor comprising an array of pixels and a substantially optically transparent layer disposed above the image sensor. The device includes an array of antennas disposed above the substantially optically transparent layer configured to receive a sample thereon. An illumination source forms part of the device and is configured to illuminate the sample. The device includes at least one processor operatively coupled to the image sensor.

In another embodiment, a system for imaging a sample includes an image sensor including an array of individual pixels and a substantially optically opaque layer disposed above the sensor array, the substantially optically opaque layer comprising an array of apertures extending therethrough, wherein a plurality of separate apertures overlie a single pixel of the sensor array. A substantially optically transparent layer is disposed over the substantially optically opaque layer, the substantially optically transparent layer configured to receive the sample thereon. The device includes a tunable illumination source configured to illuminate the sample and cast one or more shadows on the image sensor, the illumination source being tunable with respect to illumination wavelength and polarization and at least one processor configured to receive a plurality of lower resolution image frames from the sensor array at a plurality of tuned wavelengths and polarizations, wherein the at least one processor is further configured to output a high resolution image based in part on the plurality of lower resolution images.

In another embodiment, a system for imaging a sample includes a lens-based microscope configured to operate in transmission mode and a sample holder comprising a glass substrate, the glass substrate having a metallic layer disposed on a surface thereof, the metallic layer comprising an array of apertures extending through the metallic layer. The system includes a substantially optically transparent layer disposed over the metallic layer, the substantially optically transparent layer configured to receive the sample thereon. The system includes a tunable illumination source configured to illuminate the sample, the illumination source being tunable with respect to illumination wavelength and polarization.

In another embodiment, a system for imaging a sample includes a lens-based microscope configured to operate in reflection mode and a sample holder comprising a glass substrate, the glass substrate having an array of antennas disposed on a surface thereof. The system includes a substantially optically transparent layer disposed over the array of antennas, the substantially optically transparent layer configured to receive the sample thereon. A tunable illumination source configured to illuminate the sample is part of the system, the illumination source being tunable with respect to illumination wavelength and polarization.

BRIEF DESCRIPTION OF THE DRAWINGS

FIG. 4A illustrates an exemplary design of a device that includes a layer of molecules on a functionalized surface containing a plurality of apertures in a metal layer. Also illustrated in an inset view is a sample far-field diffraction pattern taken at 550 nm.

FIG. 5 illustrates a lensfree on-chip sensing setup used to detect refractive index changes.

FIG. 6A-6C illustrate, respectfully, the lensfree diffraction patterns of the aperture array sampled at z=1,100 μm for three different refractive index values: n=1.333 corresponding to de-ionized (DI) water, n+3×10$^{-3}$, and n+5×10$^{-3}$.

FIGS. 6D-6F illustrate the reconstructed transmission patterns of the same aperture array at z=~1 μm plane, right underneath the aperture region.

FIG. 7A illustrates the results of this cross correlation calculations with a dotted curve for ~2000 consecutive lensfree diffraction patterns, which were captured while the refractive index within the microchannel was changed according to the following discrete steps: (1) n=1.333, (2) n+3×10$^{-3}$, (3) n+5×10$^{-3}$, (4) n+3×10$^{-3}$, and (5) n=1.333. The solid line in FIG. 7A is a running average of the cross correlation coefficients for a window size of ~50 frames.

FIG. 7B shows the same cross correlation calculations and running average for the reconstructed transmission patterns. The intensities of the lensfree transmission patterns are normalized to the instantaneous illumination intensity, which is also detected using the same CMOS chip through a large aperture.

FIG. 10 illustrates the transmission spectra of a rectangular aperture, for different R values. A normal incidence plane wave with a polarization along x was assumed.

FIG. 11 illustrates critical parameters of a C-aperture (Left). The right side of FIG. 11 illustrates the near-field pattern of a resonant C-aperture.

FIG. 12 illustrates one example of a computer assisted design of the distribution of the apertures within one pixel for $N_1=N_2=10$.

DETAILED DESCRIPTION OF THE ILLUSTRATED EMBODIMENTS

Figure 1:
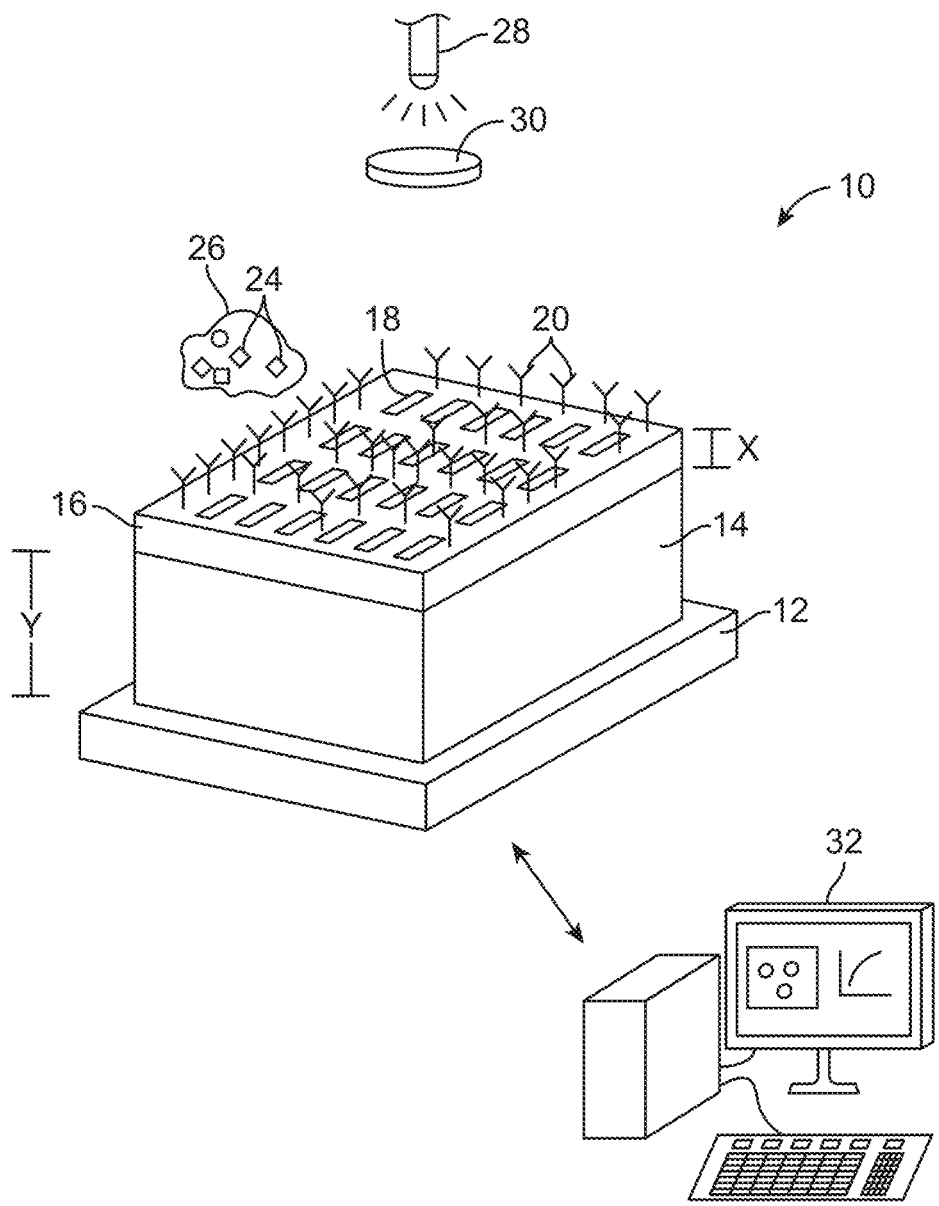
FIG. 1 illustrates a lensfree sensing device according to one embodiment. The lensfree sensing device uses a plurality of apertures formed in a metal film or layer that is disposed at a distance from an image sensor.

FIG. 1 illustrates a lensfree sensing device 10 according to one embodiment. The lensfree sensing device 10 includes an image sensor 12. The image sensor 12 preferably is a solid state imaging array. The image sensor 12 includes an array of pixels thereon and may be a charge-coupled device (CCD) or complementary metal-oxide (CMOS) based device. The image sensor 12 may be monochrome or color. The image sensor 12 generally has an active detector area that is tens or hundreds of mm$^2$ in size although a variety of sizes may be used herein. Still referring to FIG. 1, the lensfree sensing device 10 includes a substantially optically transparent layer 14 disposed above the image sensor 12. The substantially optically transparent layer 14 may comprise a solid material. Examples include glass (e.g., borosilicate glass), polymers, and the like. The substantially optically transparent layer 14 may also comprise a gap that is occupied by a gas such as air. The thickness (y) of the substantially optically transparent layer 14 generally falls within the range of 0.5 μm to more than 1000_μm. For example, a typical glass layer 14 may have a thickness around 100-200 μm. Located above the substantially optically transparent layer 14 is a substantially optically opaque layer 16. In one aspect of the invention, the substantially optically opaque layer 16 is a metallic-based layer. Herein, the substantially optically opaque layer 16 will be referred to as the metallic layer 16. The metallic layer 16 is generally thinner than the substantially optically transparent layer 14. The thickness (x) of the metallic layer 16 generally falls within the range of 10 nm to more than 1000 nm. For example, a typical metallic layer 16 may have a thickness of around 100-200 nm.

The metallic layer 16, in one embodiment as illustrated in FIG. 1, includes a plurality of apertures 18 populated therein. The apertures 18 preferably pass entirely through the metallic layer 16. The apertures 18 may be populated randomly or in patterns on the surface of the metallic layer 16. There are preferably multiple apertures 18 that overlie a single pixel of the image sensor 12. The apertures 18 may have a uniform dimension or the dimension may vary depending on the aperture 18. Typical dimensions (diameter or length) of the apertures 18 are within the range of about 5 nm to about 1000 nm. The apertures 18 are dimensioned such that plasmon waves are localized to the near-filed of the apertures 18. The apertures 18 may have a number of cross-sectional geometries. For instance, the apertures 18 may be circular, square, or rectangular as illustrated in FIG. 1.

Physical properties of these plasmonic waves, by their nature, are rather sensitive to the local refractive index of the medium surrounding the apertures 18. As the size of the metallic aperture 18 goes sub-wavelength, direct transmission of light through the aperture 18 becomes extremely inefficient and the transmission behavior of these apertures 18 starts to be dominated by plasmonic effects, exhibiting strong sensitivity to the refractive index of the surrounding medium as well as to the wavelength, polarization, and the angle of the illumination light. Nanoscale features of these metallic apertures 18 also help coupling of free space radiation into surface Plasmon waves, which can then also couple out to propagating transmission waves, enabling far-field sensing of the nearfield effects occurring at the region of the apertures 18.

The apertures 18 may be formed directly in the metallic layer 16 that is deposited on the substantially optically transparent layer 14. For example, for a substantially optically transparent layer 14 made of borosilicate glass, the metallic layer 16 (e.g., gold) may be deposited using known deposition techniques (e.g., electron beam metal deposition). The apertures 18 may then be formed in the metallic layer 16 using focused ion-beam milling (e.g., NOVA 600 NanoLab, FEI Company, Hillsboro, Oreg.). Alternatively, apertures 18 may be formed using soft-lithographic techniques to fabricate structures using elastomeric stamps, molds, or masks. With soft lithography, feature sizes of ≤100 nm can be patterned on metallic films over several centimeters of field-of-view using e.g., near-field contact-mode photolithography, which utilizes a thin elastomeric mask (polydimethylsiloxane (PDMS)) that has the designed topography on its surface and is in conformal contact with a layer of photoresist. By developing the patterned photo-resist, followed by evaporation of the metal layer and lift-off, one can fabricate the designed array of apertures 18 over several centimeters of width. Therefore, soft lithography holds a significant potential to rapidly fabricate hundreds of millions of sub-wavelength apertures 18 over centimeters of field-of-view. Some other cost-effective and high-throughput fabrication techniques that can be used include nano-imprint lithography and colloidal templating approaches.

Figure 3:
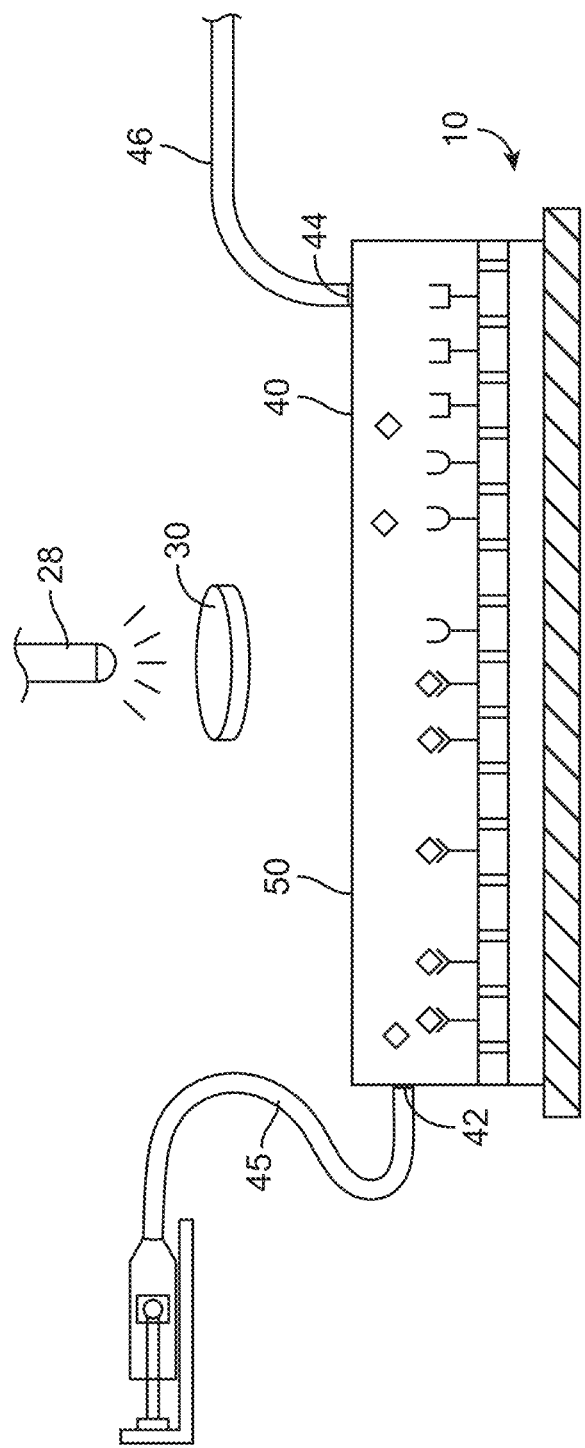
FIG. 3 illustrates an embodiment that includes a sensing device within a flow cell 40. The flow cell could also be used in conjunction with an antenna-based device.

The metallic layer 16, in one alternative embodiment, is optionally functionalized with molecules 20 directly or indirectly thereon. The molecules 20 may include, by way of illustration and not limitation, polymers, nucleic acids, antibodies, amino acids, proteins, and viruses. The molecules 20 may be bonded directly to the metallic layer 16 or to an intermediate layer such as an oxide layer 22 as illustrated in FIG. 3. Further, the molecules 20 may be secured to the metallic layer 16 via a linker molecule or the like. The molecules 20 adhered to the metallic layer 16 or intervening oxide layer 22 via a chemical bond directly or via a linker molecule as is known in the art. The molecules 20 may also be adhered by electrostatic forces as well. The molecules 20 are preferably selective to one or more target species 24. Target species 24 that bind to the molecules 20 affect the localized plasmon waves, which as explained below, affect the transmission pattern of light that passes through the apertures 18 and onto the image sensor 12. In one aspect, different locations of the metallic layer 16 may have different molecules 20 that bind to different target species 24. In this regard, a micro-array device 10 is created that is able to sense a particularized target species 24 at different known locations. A sample 26 is placed atop the metallic layer 16 directly or on top of an intervening oxide layer 22 that supports the sample 26. The sample 26 may be stationary over the device 10 or it may flow over the device 10 with a flow cell or the like as explained below in more detail.

Still referring to FIG. 1, an illumination source 28 is provided that illuminates the device 10 from the side of the device 10 with the metallic layer 16. The illumination source 28 may include a spatially incoherent quasimonochromatic illumination. For example a monochromatic light source that emits light within a relatively narrow spectral bandwidth (e.g., 20 nm) may be used. An example of an illumination source 28 that could be used include light-emitting diodes (LEDs), lasers, and the like. As seen in FIG. 1, a polarizer 30 is placed between the light source 28 and the metallic layer 16. The polarizer 30 ensures that the transmitted fields from the apertures 18 contain a single polarization component.

As seen in FIG. 1, a computer 32 interfaces with image sensor 12. The computer 32 is used to acquire and process image frames obtained from the image sensor 12. Multiple frames are transferred from the image sensor 12 to the computer and stored either permanently or temporarily for processing using one or more processors (now shown) contained in the computer 32. Specifically, the transmission patterns of the light created on the image sensor 12 are processed using phase recovery techniques to back propagate optical fields to an arbitrary depth, creating digitally focused complex transmission patterns. These patterns are then cross-correlated to enable the sensing of the localized refractive index surrounding the apertures 18. The device 10 is thus able to sense the localized natural properties of a sample 26 that is placed on the device 10. This may include fluids, cells, or other materials. In yet another embodiment as explained above, the device 10 may include a functionalized surface containing molecules 20 that are exposed to a sample 26. The molecules 20 interact with target(s) 24 therein to alter the localized refractive index at or near the location of various apertures 18. These localized changes in the refractive indices are then picked up by the changes in the transmission patterns on the image sensor 12. These changes may then indicate, for example, the binding of targets (24) to corresponding molecules 20 disposed on the device 10. The device 10 is highly sensitive to molecular binding incidents over a wide field-of-view. This enables the device 10 for label-free microarrays that are able to detect a host of target(s) 24 within a sample 26. Further, these binding incidents may be monitored and quantified in real-time with the dynamics/kinetics and the nature of attachment being evaluated over a large dynamic range. The device 10 does not need bulky and expensive optical components and can be integrated into a compact platform.

Figure 2A:
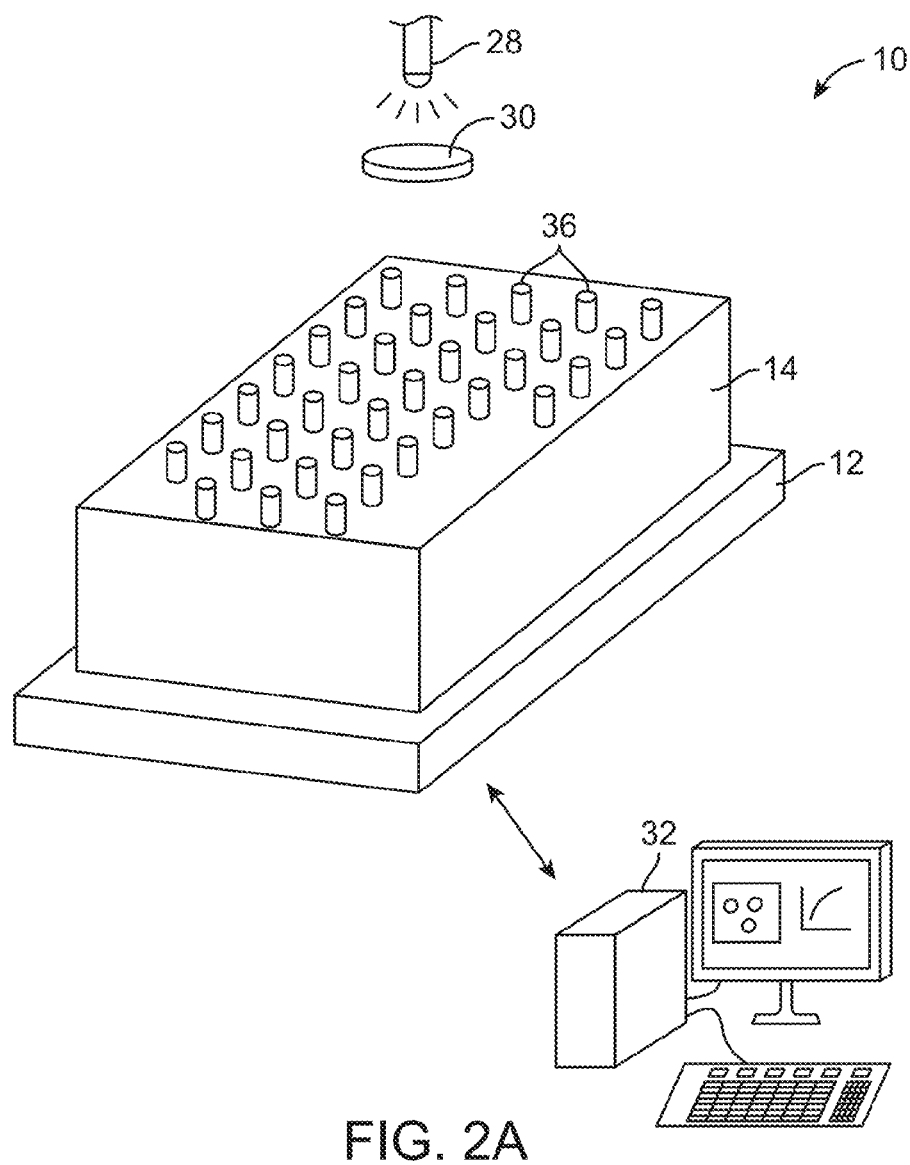
FIG. 2A illustrates an alternative embodiment of a sensing device according to another embodiment. The lensfree sensing device uses a plurality of antennas as opposed to plurality of apertures.
Figure 2B:
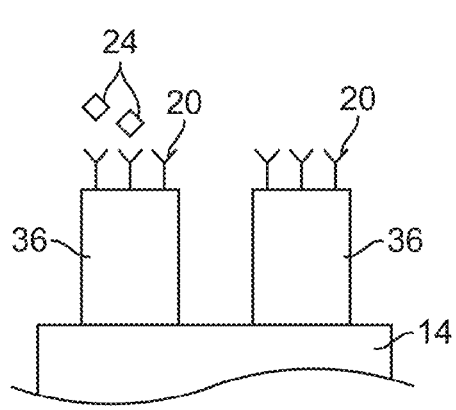
FIG. 2B illustrates a magnified view of functionalized antennas disposed atop antennas of the device of FIG. 2A.

FIG. 2A illustrates an alternative embodiment of the device 10. Other elements in this embodiment are referred to with the same reference numerals as the embodiment of FIG. 1. In the FIG. 2A embodiment, rather than have apertures 18 contained in a metallic layer 16, a plurality of antenna 36 are formed atop the substantially optically transparent layer 14. The antennas 36 are preferably sub-wavelength three dimensional structures formed from a metal. The antennas 26, for example, may include metallic rods, posts, islands or the like that are formed atop a glass transparent layer 14. The antennas 36 may be populated randomly or in patterns. Spacing between the antennas 36 is small such that plasmon waves are supported thereon. As best seen in FIG. 2B, the antennas 36 may optionally be functionalized with molecules 20 that are specific to target species 24 as in the prior embodiment. These molecules 20 may include, by way of illustration and not limitation, nucleic acids, antibodies, amino acids, proteins, and viruses. The molecules 20 may be bonded directly to the antennas 36 or to an intermediate layer such as an oxide layer. Further, the molecules 20 may be secured to the antennas 36 via a linker molecule or the like. The molecules 20 adhered to the antennas 36 via a chemical bond directly or via a linker molecule as is known in the art. The molecules 20 may also be adhered by electrostatic forces as well. The molecules 20 are preferably selective to one or more target species 24 as in the prior embodiment. Target species 24 that bind to the molecules 20 affect the localized plasmon waves, which as explained below, affects the transmission pattern of light that down onto the image sensor 12 in the free spaces located between adjacent antennas 36. In one aspect, different locations of array of antennas 36 may have different molecules 20 that bind to different target species 24. In this regard, a micro-array device 10 is created that is able to sense a particularized target species 24 at different known locations. A sample 26 is placed atop the array of antennas 26 directly or on top of an intervening oxide layer (not shown) that supports a sample 26.

FIG. 3 illustrates an embodiment that includes the device 10 within a flow cell 40. The flow cell 40 provides a fluid-sealed environment over the device 10. In this manner, fluid (e.g., sample, reagents, wash, etc.) may be flowed over the surface of the device that contains the apertures 18 or the antenna 36. The apertures 18 or antennas 36 may be optionally functionalized with molecules 20 as described herein. The flow cell 40 includes an inlet 40 and an outlet 42 that allow for the ingress and egress of fluid. As seen in FIG. 3, the inlet 40 and outlet 42 may be connected to respective conduits 45, 46. The conduits may include flexible tubing or the like. The conduit 45 connected to the inlet 40 is connected to a pump 48 that is able to pump fluid (e.g., sample, reagents, wash, etc.). In one aspect of the invention, the pump 48 is a syringe pump although other pumping devices may be used. The conduit 46 coupled to the outlet 42 may be coupled to a waste receptacle or, alternatively, the conduit 46 may be coupled to one or more devices for further processing and/or analysis.

The flow cells 40 preferably includes a top portion 50 that is substantially optically transparent such that light from the illumination source 28 is able to pass down through the flow cell 40 and onto the structured surface containing the apertures 18 or antennas 36. Materials suitable for the top portion 50 include, for example, glass and polymer materials having the ability to transmit optical radiation there through.

Still referring to FIG. 3, the flow cell 40 may be used to deliver a sample 26 to the device 10. The sample 26 may contain one or more targets 24 of interest that selective bind to molecules 20 on the optionally functionalized surface of the device 10. As stated above, the light transmitted through the apertures 18 or between the antenna 36 produce a transmission pattern onto the image sensor 12 located below. The transmission pattern, which is a diffraction pattern, contains spectral features such as texture and brightness that change in response to localized changes in the refractive index located adjacent to the surface microfeatures (i.e., apertures 18 or antenna 36). The localized changes in the refractive index may result from the bulk fluid changes in the flow cell 40 such as when one fluid is exchanged from another fluid. The localized changes in the refractive index may also happen because of binding of a target 24 with a molecule 20 contained on a functionalized surface. The refractive index may also change due to the presence of cells or other particles adjacent to the apertures 18 or antennas 36. Similarly, changes within a cell (i.e., intracellular changes) may alter the localized refractive index which may then be monitored using the transmission pattern that is cast upon the image sensor 12.

In one aspect of the invention, the various transmission patterns created by the apertures 18 or the antenna 36 will not overlap with one another and the spectral features such as texture and brightness may be monitored as a function of time without concern with respect to interference between adjacent transmission patterns. However, it is desirable to have large numbers of independent plasmonic locations places on a single device 10. In such instances, there may be a large number of apertures 18 or antenna 36 disposed above a single pixel of the image sensor 12. Here, the diffraction patterns that are cast down on the imaging sensor 12 will interfere with one another. To mitigate this challenge and thereby increase the density of the sensing locations of the device 10, an iterative phase recovery technique is used to reconstruct the complex wave corresponding to the transmission pattern of each aperture 18 or antenna 36.

In this approach, the detected lensless pattern at the imaging sensor 12 is treated as the intensity of a complex optical wave whose phase was lost during the image acquisition. To recover this lost phase, one starts with an arbitrary phase distribution at the detector plane and back propagate this complex wave to the plasmonic plane (e.g., plane with apertures 18 or antennas 36). Because the physical boundaries of the plasmonic plane (e.g., dimensions of plane containing apertures 18 or antennas 36 is known a priori, this size information can be enforced as a spatial filter for the complex fields at the plasmonic plane and forward propagate the filtered fields back to the plane of the imaging sensor 12, where the optical phase will now change to a 2D function. By replacing the intensity at the imaging sensor 12 with the measured one, and keeping the updated phase distribution, one can start the next iteration to better estimate the phase of the diffracted field after each cycle. This iterative approach rapidly converges to a unique solution after typically 10-15 iterations which take about 1 second using a standard graphics processing unit.

As explained above, the imaging sensor 12 obtains raw amplitude images of light passing through the plasmonic plane. For digital reconstruction of the diffraction patterns there are two approaches that can be used: (1) Back-propagate the Fourier components of the intensity of the diffraction pattern; and (2) Recover the 2D phase of the amplitude of each diffraction pattern. These two techniques independently enabled twin-image free reconstruction. These digital reconstruction approaches can actually be considered to be part of a broader umbrella of Interferometric and Non-interferometric Phase-Retrieval Techniques. In both of these approaches, the transfer function of the Rayleigh-Sommerfeld integral without any approximations has been used for back-propagating the fields.

The first approach mentioned above works with the intensity of the detected diffraction pattern, and is susceptible to the well-known twin image problem. To eliminate the twin image artifact in this first approach a numerical algorithm was implemented that can iteratively clean the reconstructed images from the twin image. In the second reconstruction method, the amplitudes of the lensfree diffraction pattern (rather than their intensities) are used to recover the 2D phase information of the complex diffraction field that was lost during the detection process. This phase recovery step is further useful as it can be utilized for characterization of a heterogeneous solution overlying the apertures 18 or antenna 36. Once the entire complex diffraction field is recovered, the microscopic image can be calculated without any twin image artifact through back-propagation of the complex field.

The phase recovery approach treats the detected quantity as the amplitude of a complex diffraction field, and tries to iteratively recover its phase for digital reconstruction. Therefore the phase recovery based reconstruction approach is especially useful for where the cross-interference terms start to dominate over holographic diffraction. As a trade-off, the space-bandwidth product that is required at the detector end is increased by two fold for the phase recovery technique when compared to the first approach, since the latter one does not only deal with the holographic diffraction term, but also deals with self-interference terms.

The reconstruction process can utilize successive fast Fourier transform (FFT) operations, where after the initial FFT of each iteration, transfer function of Rayleigh-Sommerfeld integral without any approximations has been applied to the Fourier components of the diffraction pattern. Because FFT is used, the presented recoveries are also quite fast in terms of digital computation time, with a convergence time of less than a few of seconds using e.g., a 1.6 GHz Pentium Processor.

In order to diffract the wavefronts, the angular spectrum approach is used to numerically solve the Rayleigh-Sommerfeld integral. This computation involves multiplying the Fourier transform of the field with the transfer function of propagation through linear, isotropic media, as shown below:

$$H_z(f_x, f_y) = \begin{cases} \exp(j2\pi z \frac{n}{\lambda})\sqrt{1-(\lambda f_x/n)^2-(\lambda f_y/n)^2}, & \sqrt{f_x^2+f_y^2} < \frac{n}{\lambda} \\ 0, & \text{otherwise} \end{cases} \quad \text{Eq. (1)}$$

where $f_x$ and $f_y$ are the spatial frequencies and n is the refractive index of the medium.

Two different iterative approaches, as explained above, can be taken in order to reconstruct the image to the plasmonic plane, free from any twin-image artifact. In both methods, the raw diffraction patterns are up-sampled typically by a factor of four to six, using cubic spline interpolation before the iterative reconstruction procedure. Although up-sampling does not immediately increase the information content of the diffraction patterns, it still offers significant improvements for achieving a more accurate phase recovery and higher resolution in the reconstructed image. Through the iterative reconstruction steps detailed below, these higher spatial frequencies gradually attain non-zero energy, which allows sub-pixel resolution in the final reconstruction.

Method 1:

The first method falls under the broad category of Interferometric Phase-Retrieval Techniques and is applicable to cases where the recorded intensity is dominated by the holographic diffraction terms. The first step is the digital reconstruction of the hologram, which is achieved by propagating the hologram intensity by a distance of $z_2$ away from the hologram plane yielding the initial wavefront $U_{rec}$. As a result of this computation, the virtual image of the object is recovered together with its spatially overlapping defocused twin-image. It is important to note that the recorded intensity can also be propagated by a distance of $-z_2$. In this case, the real image of the object can be recovered, while the defocused virtual image leads to the twin-image formation.

In order to eliminate the twin-image artifact, an iterative approach using finite support constraints is utilized. Essentially, this technique relies on the fact that duplicate information for the phase and amplitude of the plasmonic plane exists in two different reconstruction planes at distances $+z_2$ and $-z_2$ from the hologram plane, where the virtual and real images of the object are recovered, respectively. Therefore, a twin-image-free reconstruction in one of the image planes can be obtained, while filtering out the duplicate image in the other plane. Without loss of generality, the real image was filtered out to obtain a twin-image-free reconstruction in the virtual image plane at $-z_2$. The real image of the plasmonic plane only occupies the region inside its support (e.g., physical boundaries of plasmonic surface), while the defocused twin-image image spreads out to a wider region around the object, also overlapping with the real image inside the support. Hence, deleting the information only inside the support ensures that the real image is completely removed from the reconstructed wavefront. Nevertheless, the virtual image information inside the support is also lost, and the iterative technique tries to recover the missing information of the virtual image by going back and forth between the virtual and real image planes, recovering more of the lost information at each iteration.

The steps of twin-image elimination are detailed below.

a) Initially the real image, which is the back-projected hologram at a distance of $+z_2$, is used for determining the object support. Object support can be defined by either thresholding the intensity of the reconstructed image, or searching for its local minima.

b) The region inside the support is deleted and a constant value is assigned to this region as an initial guess for the deleted part of the virtual image inside the support as shown below:

$$U_{z_2}^{(i)}(x,y) = \begin{cases} U_{rec}, & x,y \notin S \\ \overline{U}_{rec}, & x,y \in S \end{cases} \quad \text{Eq. (2)}$$

Where $U_z^{(i)}(x,y)$ denotes the field at the real image plane after the $i^{th}$ iteration. S represents the area defined by the object support, and $\overline{U}_{rec}$ is the mean value of $U_{rec}$ within the support.

c) Then, the field at the real image plane is back propagated by $-2z_2$ to the virtual image plane. Ideally, the reconstruction at this plane should be free from any twin-image distortions. Therefore, the region outside the support can be set to a d.c. background value to eliminate any remaining out-of-focus real image in the virtual image plane. However, this constraint is applied smoothly as determined by the relaxation parameter $\beta$ below, rather than sharply setting the image to d.c. level outside the support:

$$U_{-z_2}^{(i)}(x,y) = \begin{cases} D - \dfrac{D - U_{-z_2}^{(i)}}{\beta}, & x,y \notin S \\ U_{-z_2}^{(i)}, & x,y \in S \end{cases} \quad \text{Eq. (3)}$$

where D is the background in the reconstructed field, which can either be obtained from a measured background image in the absence of the object, or can simply be chosen as the mean value of the field outside the object supports at the virtual image plane. $\beta$ is a real valued parameter greater than unity, and is typically chosen around 2-3. Increasing $\beta$ leads to faster convergence, but compromises the immunity of the iterative estimation accuracy to background noise.

d) The field at the virtual image plane is forward propagated to the real-image plane, where the region inside the support now has a better estimate of the missing part of the virtual image. The region outside the support can be replaced by $U_{z_2}^{(1)}(x,y)$, the original reconstructed field at the real image plane, as shown below:

$$U_{z_2}^{(i+1)}(x,y) = \begin{cases} U_{z_2}^{(1)}, & x,y \notin S \\ U_{z_2}^{(i+1)}, & x,y \in S \end{cases} \quad \text{Eq. (4)}$$

Steps c to d can be repeated iteratively until the final image converges. By replacing the intensity at the detector plane with the measured one, and keeping the updated phase distribution, one can start the next iteration to better estimate the phase of the diffracted field after each cycle. Convergence is achieved after 10-15 iterations, which takes much less than a minute on a computer with a modest hardware configuration.

Method 2:

The second method utilized for eliminating the twin-image is classified under Non-Interferometric Phase-Retrieval Techniques, where the recorded image is treated as the intensity of any diffraction field. Together with the constraint that the imaging field has finite support, this technique is capable of iteratively recovering the phase of the diffracted field incident on the detector from a single intensity image. As a result, the complex field (amplitude and phase), rather than the intensity, can be back-propagated, thereby allowing reconstruction of the objects free from any twin-image contamination. This method can be decomposed into the following steps:

a) The square-root of the recorded diffraction pattern intensity is propagated by a distance of $-z_2$ to the cell plane, assuming a field phase of zero as an initial guess. The aim of the algorithm is to iteratively determine the actual phase of the complex field at the detector plane, and eventually at the plasmonic plane. In the first iteration, the object support is defined either by thresholding the intensity of the field at the plasmonic plane, or by locating its regional maxima and/or minima.

b) The field inside the object supports is preserved, while the complex field values outside the supports is replaced by a background value $D_{-z_2}(x,y)$, as shown below:

$$U_{-z_2}^{i+1}(x,y) = \begin{cases} m \cdot D_{-z_0}(x,y), & x,y \notin S \\ U_{-z_2}^{i}(x,y), & x,y \in S \end{cases} \quad \text{Eq. (5)}$$

where $D_{-z_2}(x,y)$ is obtained by propagating the square root of the background intensity of the image obtained by the same setup in the absence of the cells; and $m=\text{mean}(U_{-z_2}^i(x,y)/\text{mean}(D_{-z_2}(x,y))$.

c) The modified field at the plasmonic plane is propagated back to the detector plane, where the field now has a non-zero phase value. The amplitude of this field is replaced with the square root of the original recorded hologram intensity as no modification for the amplitude should be allowed while converging for its phase. Consequently, $U^{(i)}_0(x,y)$, the complex diffraction field at the detector plane after the $i^{th}$ iteration can be written as follows:

$$U^{(i)}_0(x,y)=|U^{(0)}_0(x,y)|\cdot\exp(\varnothing^{(i)}_0(x,y)) \quad \text{Eq. (6)}$$

where the superscripts denote the iteration step, and $\varnothing^{(i)}_0(x,y)$ denotes the phase of the field after the $i^{th}$ iteration.

Steps a to c can be iterated until the phase recovery converges. Typically, the results presented in this paper are obtained with less than 15 iterations, which is quite similar to the first Method.

Additional details regarding the phase recovery technique used to reconstruct the complex wave corresponding to the transmission pattern of created from each aperture 18 or antenna 32 may be found in the following publications which are incorporated by reference as if set forth fully herein: C. Oh et al., *On-chip differential interference contrast microscopy using lensless digital holography*, Opt. Express 18, 4717-26 (2010); O. Mudanyali et al., *Compact, light-weight and cost-effective microscope based on lensless incoherent holography for telemedicine applications*, Lab Chip 10, 1417-28 (2010); and D. Tseng et al., *Lensfree microscopy on a cellphone*, Lab Chip 10, 1787 (2010).

FIG. 4A illustrates an exemplary design of a device 10 that includes an image sensor 12 having individual pixels 13 sized at around 2 μm. A substantially optically transparent layer 14 (e.g., glass) is disposed on the active side of the image sensor 12 (which could be upper or lower side as the case may be). The substantially optically transparent layer 14 has a thickness of around 100 μm although other thicknesses are possible. A metallic layer 16 is disposed on the substantially optically transparent layer 14 and has a thickness of around 200 nm. The metallic layer 16 contains thousands of apertures 18 (some of which are illustrated in FIG. 4A) which act collectively. The apertures 18 shown with a layer containing molecules 20 that is configured to detect molecular binding events occurring less than 20 nm away from the surface of the metallic layer 16. As seen in FIG. 4A, a solution 25 (e.g., water-based solution) is exposed to the active surface of the metallic layer 16. An illumination source 28 emits radiation which passes through the solution 25 and onto the metallic layer 16. Light passes through the apertures 18 to create a transmission pattern which is detected by the image sensor 12. FIG. 4A illustrates a sampled 2D far-field transmission pattern A taken at a wavelength of 550 nm.

Figure 4B:
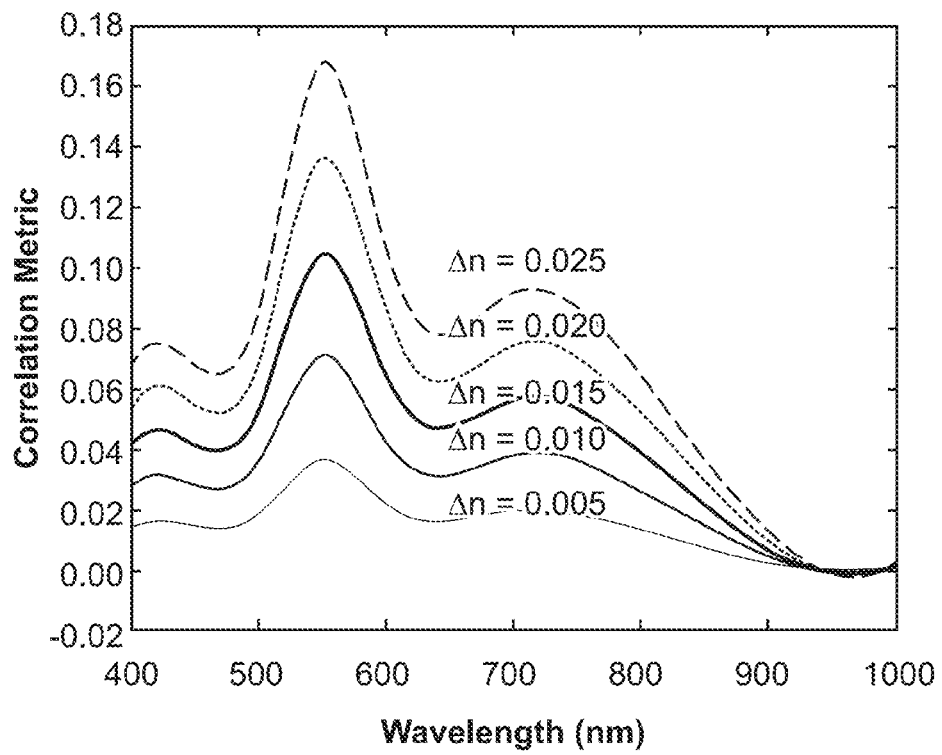
FIG. 4B illustrates a graph of a 2D correlation metric calculated for various illumination wavelengths for the 2D far-field pattern that is sampled at the image sensor in the device of FIG. 4A.
Figure 4C:
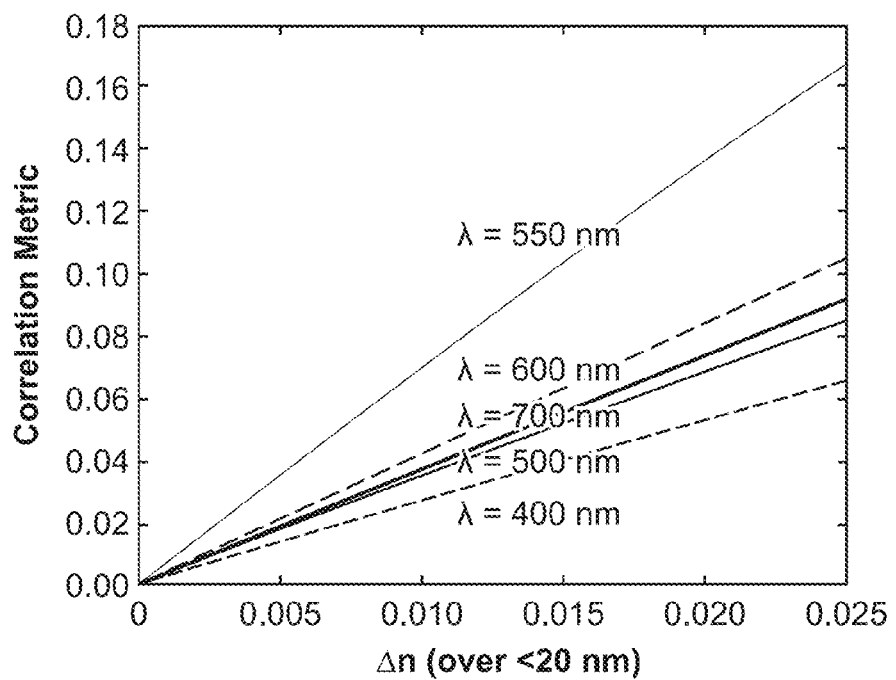
FIG. 4C illustrates the 2D correlation metric as a function of change refractive index ($\Delta n$).

FIG. 4B illustrates a graph of a 2D correlation metric calculated for various illumination wavelengths for the 2D far-field pattern that is sampled at the image sensor 12. Results were obtained using Finite-Difference Time-Domain (FDTD) numerical simulation. As seen in FIG. 4B, a wavelength of around 550 nm exhibits the best sensitivity. FIG. 4C illustrates the 2D correlation metric as a function of change refractive index (Δn). The curve with the highest slope, and thus sensitivity, is seen for incident radiation with a wavelength of around 550 nm. In this example, a refractive index change of about 0.001 that occurs at the surface at a distance of less than 20 nm away from the apertures 18 can be detected. A reasonable signal-to-noise (SNR) ratio of less than 17 dB has been assumed in the numerical simulation.

To find the difference between two diffraction patterns a correlation metric, $C_{rc}$, is used which can be calculated as follows, $$C_{rc} = \frac{\sum_m \sum_n (X_{rc})}{\sum_m \sum_n (X_{rr})} \quad \text{Eq. (7)}$$

where $X_{ij}$ represents the 2-dimensional cross correlation pattern of the reference (i-th image) and the diffraction pattern belonging to other part of the structured substrate (j-th image), and m,n are integer numbers indicating the pixel locations in the intensity images.

EXPERIMENT

Lensfree Sensing of Refractive Index Changes

FIG. 5 illustrates a lensfree on-chip sensing setup used to detect refractive index changes. A plasmonic aperture array, as shown in the SEM image on the top right corner of FIG. 5, is illuminated with a quasimohochromatic source (e.g., 550 nm center wavelength with ~20 nm bandwidth) located ~10-30 cm away (H) from its surface. The lensfree transmission pattern of this plasmonic structure is sampled by a CMOS chip placed at z~1 mm away from the aperture plane. The surface 52 indicates the detector active area (~6×4 mm²). The plasmonic aperture array (B) shown above is composed of uniformly spaced slits each with a length of ~6 μm where the slit width varied (from left to right) between ~80 and ~200 nm in discrete steps of ~20 nm. The physical gap between two neighboring slits is kept constant at ~200 nm.

To implement the above discussed lensfree on-chip sensing architecture, a plasmonic aperture array design was employed that, as discussed above, is composed of varying widths of rectangular sub-wavelength apertures/slits spanning an area of ~14×14 μm² as illustrated in FIG. 5 (other dimensions could be used). In this design, the function of this array of sub-wavelength slits with varying widths was to introduce different diffraction patterns as a function of the local refractive index. This plasmonic (illustrated in FIG. 5) structure was fabricated using focused ion-beam milling (NOVA 600) on borosilicate cover slips (150 μm thick) that were coated with ~200 nm gold layer using electron beam metal deposition (CHA Mark40).

The prepared chip was then used as the bottom substrate of a custom designed microfluidic device as illustrated in FIG. 5. The liquid samples having different refractive indices were flushed into the microfluidic chamber or flow cell 40 to interact with the near-field of the apertures by means of an automated syringe pump. Fluid passed into inlets 42 and exited via outlets 44. Lensfree diffraction patterns corresponding to each refractive index value were continuously captured on a chip at a frame rate of ~2-3 fps using a CMOS image sensor while the liquid was flowing through the microfluidic channel. The illumination was achieved using a monochromator at 550 nm with a spectral bandwidth of ~20 nm, which indicates that a standard light-emitting diode could also be used in terms of both spatial and temporal coherence properties. An inexpensive plastic polarizer (not shown but similar to polarizer 30 of FIG. 1) was used in front of the illumination source to create a linear polarization that is orthogonal to the slit direction. This ensured that the transmitted fields from the plasmonic apertures contained only a single polarization component, To experimentally validate the sensitivity of this lensfree platform, salt-water was used with well-controlled concentrations such that the exact value of the liquid refractive index could be extracted from a look-up table. FIGS. 6A, 6B, and 6C illustrate the lensfree diffraction patterns of the aperture array sampled at z=1,100 μm for three different refractive index values, n=1.333 corresponding to de-ionized (DI) water, $n+3\times10^{-3}$, and $n+5\times10^{-3}$, respectively. FIGS. 6D, 6E, and 6F illustrate the reconstructed transmission patterns of the same aperture array at z=~1 μm plane, right underneath the aperture region.

To better quantify the numerical differences among these lensfree diffraction patterns and relate them to refractive index changes (Δn) within the microchannel the 2D cross correlation coefficients were calculated between the first lensfree pattern (corresponding to DI water) and the rest of the acquired diffraction images. FIG. 7A illustrates the results of this cross correlation calculations with a dotted curve for ~2000 consecutive lensfree diffraction patterns, which were captured while the refractive index within the microchannel was changed according to the following discrete steps: (1) n=1.333, (2) $n+3\times10^{-3}$, (3) $n+5\times10^{-3}$, (4) $n+3\times10^{-3}$, and (5) n=1.333. The solid line in FIG. 7A is a running average of the cross correlation coefficients for a window size of ~50 frames. FIG. 7B shows the same cross correlation calculations and running average for the reconstructed transmission patterns. The intensities of the lensfree transmission patterns are normalized to the instantaneous illumination intensity, which is also detected using the same CMOS chip through a large aperture.

As illustrated in these results, by recording the lensfree diffraction patterns of this plasmonic aperture array on a compact chip one can faithfully track refractive changes as small as $\Delta n=2\times10^{-3}$. To further validate the results, FDTD simulations were performed of the same plasmonic structure, the results of which are summarized in FIG. 8. According to these FDTD simulations, the far-field lensfree diffraction patterns of the aperture array closely match the experimental results presented in FIGS. 6A-6F and 7A and 7B. Furthermore, the same FDTD results also indicate that, as desired, the response of the 2D cross correlation coefficient of these lensfree diffraction patterns is linear over a large refractive index range spanning 1.33-1.35.

While these experimental and FDTD simulation results both demonstrate the useful sensitivity of the proposed lensfree on-chip sensing scheme, there is still room for further improvement that can be implemented by utilizing more advanced digital processing of these diffraction patterns. In particular, due to its lensfree operation, the sampled transmission patterns of the plasmonic aperture array spread over a large area on the sensor chip. While this has no negative consequences for a low number of spots on the same chip, it would create significant limitations as one aims to increase the density and hence the throughput of sensing. In other words, as more and more independent plasmonic spots are placed on the same chip (e.g., toward a label-free DNA or protein microarray design), their lensfree diffraction patterns will overlap with each other at the detector, which would degrade the sensitivity of the lensfree sensing platform.

To mitigate this challenge and increase the density of the sensing spots on the same microfluidic chip, the iterative phase recovery technique discussed herein was used to reconstruct the complex wave corresponding to the transmission pattern of each aperture array. In this numerical approach, the detected lensless pattern is treated as the intensity of a complex optical wave whose phase was lost during the image acquisition. To recover this lost phase, first start with an arbitrary phase distribution at the detector plane and back propagate this complex wave to the plasmonic aperture plane. Since the physical boundaries of the aperture region (e.g., ~14×14 μm² in FIG. 5) is known a priori, one can enforce this size information as a spatial filter for the complex fields at the aperture plane and forward propagate the filtered fields back to the detector plane, where the optical phase will now change to a 2D function. By replacing the intensity at the detector plane with the measured one, and keeping the updated phase distribution, one can start the next iteration to better estimate the phase of the diffracted field after each cycle. This iterative approach rapidly converges to a unique solution after typically 10-15 iterations which take less than 1 second using a standard graphics processing unit.

Figure 8:
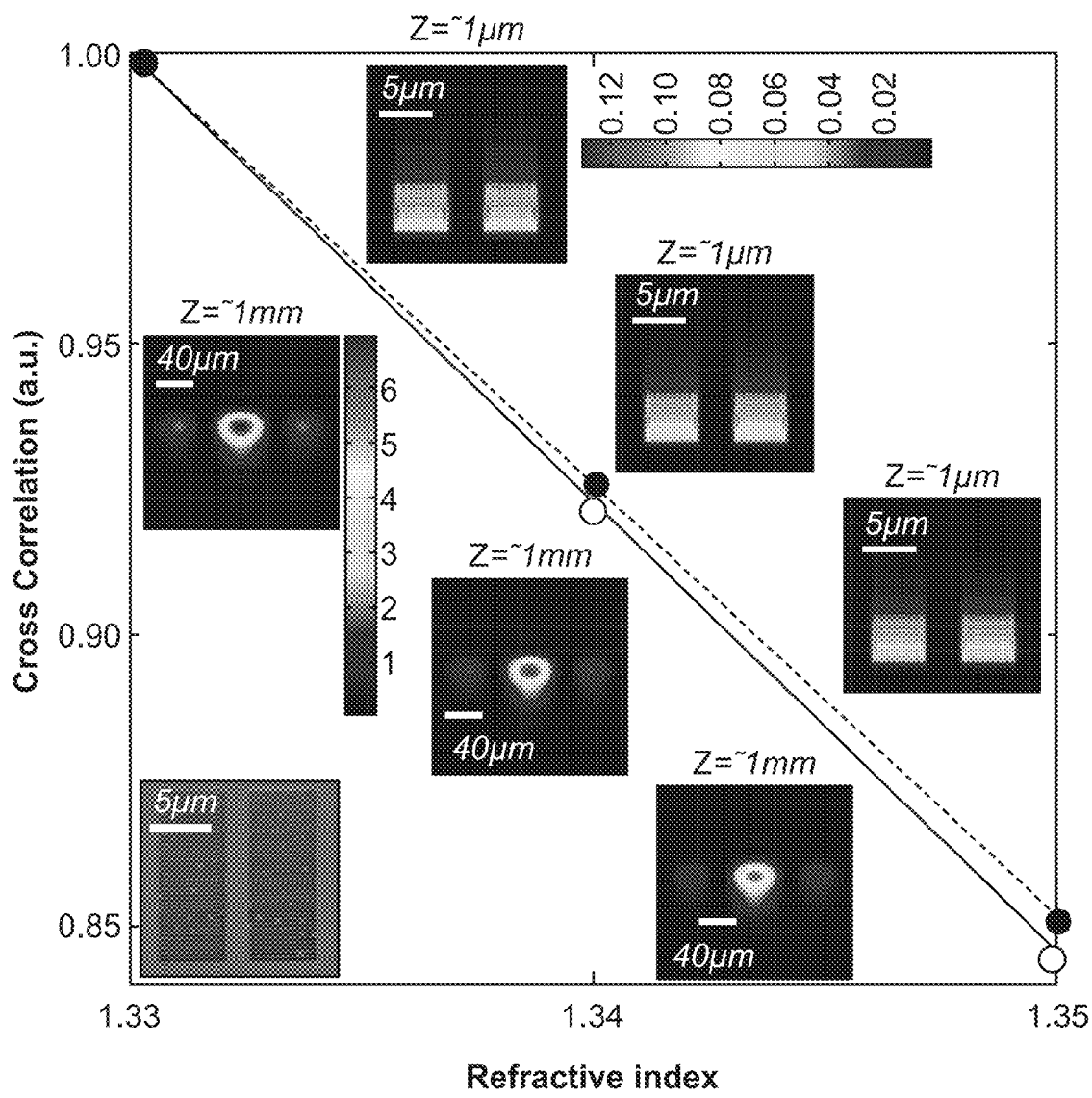
FIG. 8 illustrates the cross correlation coefficients among lensfree transmission patterns of the same aperture array shown in FIGS. 5 and 7A based on FDTD simulation results and are calculated as a function of the refractive index within the microchannel. These calculations were performed for both z=~1 mm (solid line) and z=~1 μm (dashed line) planes. Insets depict the 2D transmission patterns for three different refractive index values (1.33, 1.34, and 1.35, respectively), where the upper (lower) ones are calculated at z=~1 μm (z=~1 mm).

FIGS. 6D-6F illustrate the iterative reconstruction results of the field intensity at the plasmonic aperture plane using the raw lensfree diffraction patterns shown in FIGS. 6A-6C. If the 2D cross correlation coefficients are calculated among these reconstructed patterns, one obtains updated sensing curves as illustrated in FIG. 7B. Once again, similar to FIG. 7A, the device and method can faithfully track refractive changes as small as $\Delta n=2\times10^{-3}$, this time using the reconstructed optical intensity patterns at the aperture plane. The major advantage of this phase recovery based approach is that it enables multiplexing more densely packed plasmonic spots such that the overall throughout of on-chip sensing can be significantly increased without affecting the sensitivity of the platform. The FDTD simulations which calculate the field patterns close to the aperture plane as illustrated in FIG. 8, nicely match to the experimental results.

The above-discussed iterative phase recovery approach works even if the diffraction patterns of neighboring plasmonic spots overlap at the detector plane (FIGS. 6D-6F), where the transmission patterns of the top and bottom aperture arrays are resolved from each other, which normally were entirely overlapping at the detector plane as shown in FIGS. 6A-6C. In addition to this, as the sensing field of view increases to cover the entire detector active area (e.g., >20 mm²), the requirements for spatial and temporal coherence of illumination would not change, which is quite important for scaling this platform to extreme throughputs without changing the illumination conditions. The exact value of the spatial coherence diameter in the lensfree platform can be precisely be tuned by controlling the aperture size of the source or by controlling the propagation distance between the source and the plasmonic aperture planes.

It should be noted that fabrication imperfections of the plasmonic nanostructures in the design do not constitute a fundamental challenge in the lensfree on-chip sensing approach, since it is effectively measuring the cross correlation variations of the lensfree diffraction patterns of the plasmonic apertures as function of the local refractive index. This differential correlation measurement makes this scheme robust to potential fabrication imperfections, which is especially important for wide field of view implementations of this platform for increased throughput in sensing.

With reference to the embodiments described in FIGS. 1-7B, the computer 32 containing one or more processors contained therein is configured to reconstruct the transmission (e.g., diffraction) patterns at or near the aperture or antenna plane based on the patterns received at the image sensor 12. The computer 32 or the processor(s) contained therein are also configured to calculate and output a correlation coefficient. The correlation coefficient may be measured by comparison of the transmission pattern between one or more transmission patterns (e.g., first transmission pattern compared with subsequent transmission patterns). As one example, a sample having a known index of refraction can be used as the basis of the correlation coefficient (e.g., DI water used as the basis of comparison and has cross-correlation of unity).

In one aspect of the invention, a calibration curve or the like may be generated that correlates the cross-correlation values with a particular index of refraction. In this regard, the cross-correlation value may be used as a threshold value to determine not only a particular index of refraction but also some other material property. In this regard, cross-correlation value may be monitored and associated with a particular material property (e.g., index of refraction). The cross-correlation may also be monitored to detect some other property such as the binding of target molecules 24 to a functionalized surface 20. In this example, when the cross-correlation value hits a certain threshold value, this indicates the binding of target molecules 24 to the functionalized surface 20. Cross-correlation or index of refraction is thus used as a proxy to determine the state or some other property occurring adjacent to the plane containing the apertures 18 or the antennas 36.

FIGS. 9A-9C, 10, 11, 12, 13A, and 13B pertain to other embodiments of the invention that utilizes a metallic layer with apertures (or antennas) for an imaging purposes. For a microscopy system that involves use of lenses, the optical magnification at the image plane has to be designed such that the pixel size of the recording medium (e.g., a charge-coupled device (CCD)) is much smaller than the width of the point-spread function associated with the numerical aperture (NA) of the system. In this embodiment, which does not suffer from this deficiency, the object of interest is positioned onto the active region of a specially designed chip that includes a metal layer containing apertures therein. Therefore, in this imaging modality: (1) there is no optical magnification; and (2) spatial resolution is not determined only by the NA of the system.

Figure 9A:
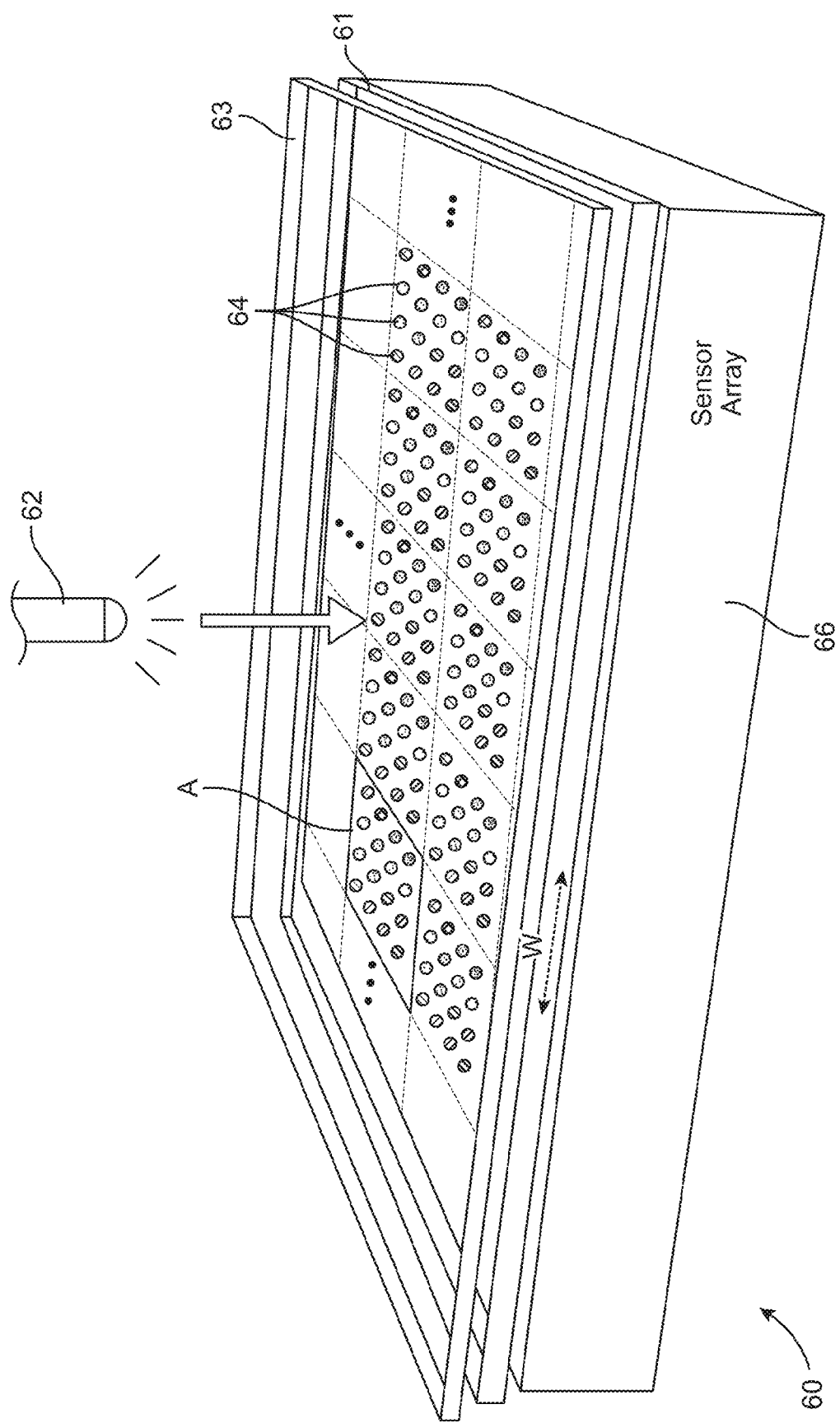
FIG. 9A illustrates another embodiment of a device for imaging, where the object to be imaged (e.g., cells within a microfluidic device) is positioned directly onto a specially designed sensor chip.

FIG. 9A illustrates a schematic representation of one possible configuration, where the object to be imaged (e.g., cells within a microfluidic device) is positioned directly onto a specially designed sensor chip 60; and the illumination of the object is achieved by using a tunable light source 62, i.e., the wavelength and polarization is scanned as a function of time. For a regular CCD technology, the pixel size (W) at the sensor is typically ~5-10 μm which implies that without using any lenses the resolution is limited to >5 μm. In this embodiment, the limiting effect of the pixel size on resolution is removed by fabricating an array of uniquely different apertures 64 within the area A of each pixel of the image sensor 66. Each "A" area is repeated across the surface of the metal layer 61. An oxide layer 63 is disposed above the apertures 64. The apertures 64 are sub-wavelength in size having nanometer-sized dimensions.

Figure 9B:
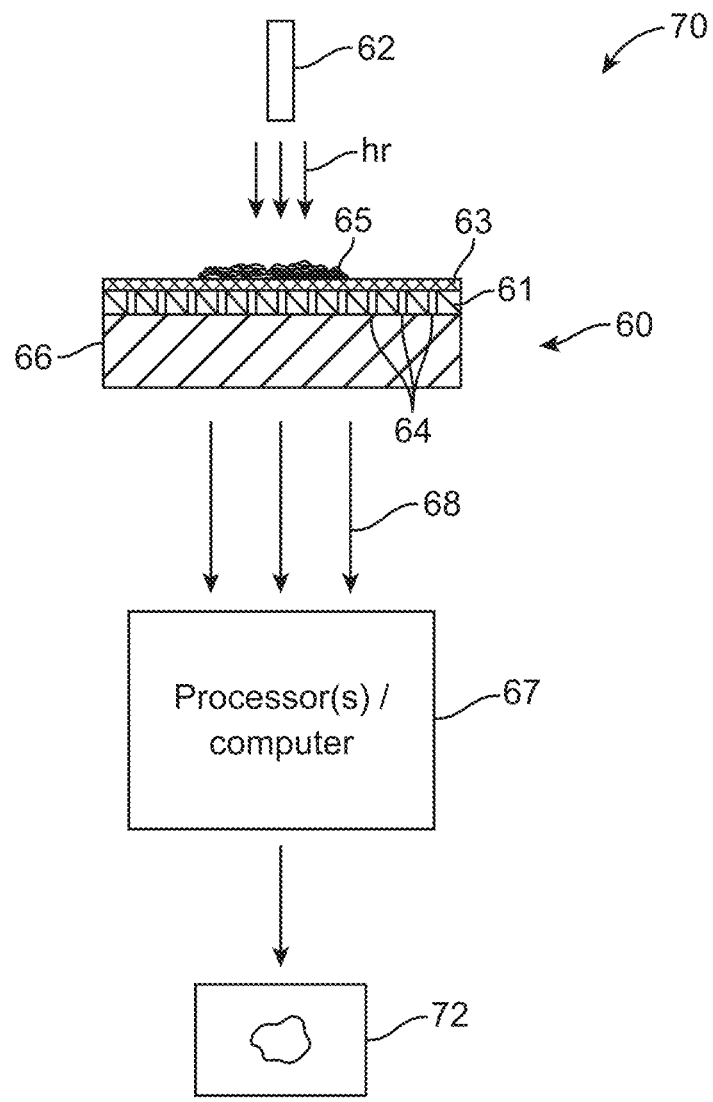
FIG. 9B illustrates an imaging system that includes a chip like that illustrated in FIG. 9A.

FIG. 9B illustrates an imaging system 70 that includes the chip 60. The chip 60 includes an imaging sensor 66 that may be a CMOS or CCD based. The imagine sensor 66 may include a 100% optical fill factor CCD chip. A metal layer 61 is disposed on the imaging sensor 66 and the metal layer 61 includes apertures 64 formed therein. The metal layer 61 may be coated with an oxide layer 63 that will support a sample 65. The tunable light source 62 is configured to illuminate the sample 65. Multiple low resolution images 68 obtained from the imaging sensor 66 are transferred to a computer 67 that contains one or more processors that are configured to output a high resolution image 72.

Before the fabrication of the designed aperture array, the image sensor 66 will initially be coated by a thin transparent layer of oxide (e.g., <20 nm $SiO_x$) to passivate the active region of the CCD chip. This step is actually not needed for most commercially available CCD chips since they already have on the active region such a thin passivization layer. Next, the passivated surface of the image sensor 66 will be coated with an opaque layer of thin metallic film 61 (e.g., ~100 nm Al). This may be through e-beam or thermal evaporation. The thickness of the metallic film 61 on the image sensor 66 determines the depth of the apertures 64. To increase the light transmission for the resonant apertures, a thickness value as small as possible can be chosen that still acts as an opaque layer. This implies that a thickness of ~100-200 nm would be appropriate for the evaporated metallic layer. Al thin films may be preferred to Au or Ag because of their lower surface plasmon propagation length which helps to isolate one aperture 64 from the other apertures 64 within the same pixel.

Following the metal evaporation step, the designed aperture array will be fabricated onto the metallic surface 61 using e.g., electron beam lithography. Focused ion beam (FIB) milling could also be used to fabricate the designed aperture array. This second approach involves a simpler fabrication; however, the FOV will be practically limited to ~200 μm×200 μm due to slower speed of the aperture writing (e.g., ~1 min of FIB time would be used for each pixel of the sensor array for $N_1=N_2=10$). An alternative approach to fabricate the designed aperture array could be the use of soft-lithography. The major advantages of this approach over electron beam lithography or FIB are its simplicity, low-cost and speed. With soft lithography, feature sizes of ≤100 nm could be patterned on metallic films over a large FOV (>1 cm²) using e.g., near-field contact-mode photolithography, which utilizes a thin elastomeric mask (polydimethylsiloxane (PDMS)) that has the designed topography on its surface and is in conformal contact with a layer of photoresist. By developing the patterned photoresist, followed by evaporation of the metal layer and lift-off, one can fabricate the designed aperture array onto the sensor plane over an area of >5 mm². Therefore, soft lithography can potentially be used to replace the more complex and expensive fabrication steps of electron beam lithography or FIB milling.

To align the aperture array with respect to the pixel edges, several marks will be placed to the edges of the image sensor 66 to define the start of a pixel. Once the apertures 64 are opened, a thin transparent layer of oxide 63 (e.g., ~50-100 nm $SiO_x$) will be deposited onto the metal film 61 using reactive ion sputtering or thermal evaporation. The function of this transparent layer will be to isolate the apertures from the near-field of the object, i.e., the resonant behavior of the designed apertures is not affected by the presence of different objects that are placed onto the oxide layer. At this final step, a more complex fabrication recipe can be used to deposit more than one type of oxide material, e.g., $SiO_x$ and $TiO_x$. The different dielectric constants of these materials can be used to tune the resonance of the apertures, helping to further reduce the cross-talk among different apertures on the chip. One simple fabrication method to vary the dielectric constant of the apertures 64 could be to open some of the apertures using e.g., FIB milling, after an oxide layer (e.g., ~100 nm $SiO_x$) has been deposited onto the aperture plane. This simple strategy will result in some of the apertures 64 to be filled with air while some others with $SiO_x$, which results in an additional degree of freedom to tune the resonance condition.

Figure 9C:
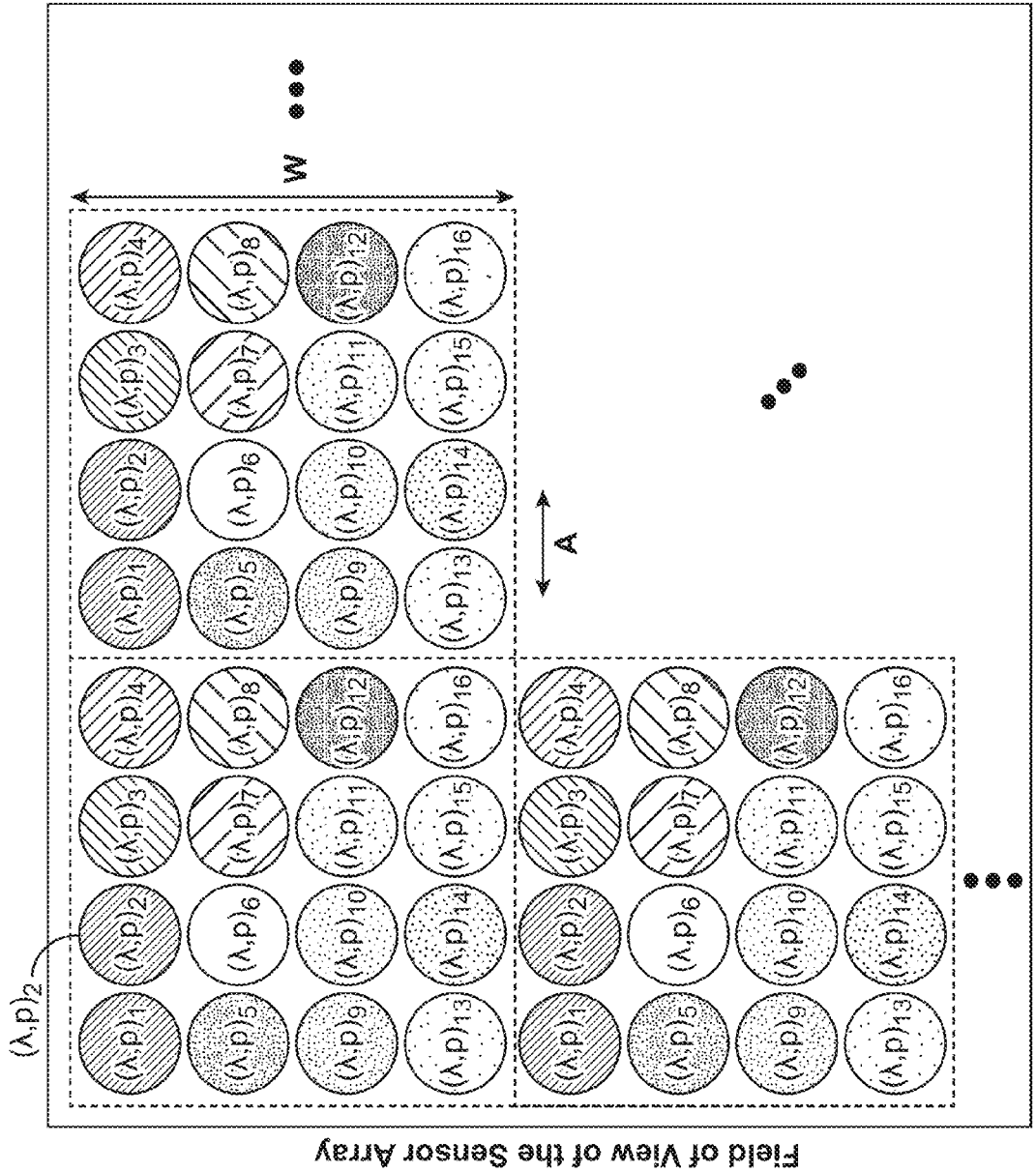
FIG. 9C illustrates a top down view of the field of view of an image sensor illustrating individual apertures (or antenna as the case may be) within a series of repeating arrays. Each aperture (or antenna) is resonant at a particular wavelength and polarization.

The key property of the aperture array within each pixel area is that each sub-wavelength aperture 64 of the array will be different in its shape, size and orientation such that it exhibits a resonant transmission only at a desired wavelength and polarization combination, $(\lambda,p)n$, where $\lambda$ is the illumination wavelength, and p is the polarization. The remaining apertures 64 within the same pixel area will all be non-resonant at that particular $(\lambda,p)n$, and since they have sub-wavelength dimensions, their transmission at $(\lambda,p)n$ will all be negligible. Therefore, the transmitted light to the active area of each pixel will only have photons originating from the resonant structure. This same aperture array will then identically be copied to the remaining pixels of the sensor array as illustrated in FIG. 9C (showing three such identical arrays of 4×4). The field of view of the chip 60 will thus contain a plurality of similar arrays where each single array has apertures 64 with differing resonant properties.

In the setup of FIGS. 9A and 9B, the object will then be directly positioned onto the oxide layer 63, and will be illuminated by a tunable light source 62, where the shadow of the object will be sampled by the aperture array. By changing $(\lambda,p)n$, one can effectively scan the entire area of the sensor chip 60, with a scanning step size that equals to the distance between two neighboring apertures (i.e., A in FIG. 9C). Assuming an array of $N_1 \times N_2$ apertures per each pixel, this embodiment requires capturing of $N_1 \times N_2$ different frames from the sensor, each of which corresponds to a different $(\lambda,p)_n$. Thus, by digitally combining these $N_1 \times N_2$ frames, one can improve the resolution to be $N_1$ and $N_2$ times better than the pixel width of the sensor along each direction (x and y) would normally permit. For a CCD chip 60 with a pixel size of ~5 μm and a 100% optical fill factor (i.e., entire area of the chip is used to detect photons), by having $N_1=N_2=10$, this embodiment can achieve a resolution of ~500 nm over the entire FOV of the sensor chip 60. Therefore, for an FOV of ~1 $mm^2$, a total of 100 frames need to be collected from the image sensor 66. With a moderate read-out rate of ~100 frames/sec for 1 $mm^2$ FOV, the total image acquisition time can be ~1 second, implying a typical imaging speed of ~60 $mm^2$/min.

A monochrome CCD chip may be used (e.g., Dalsa FT50M or KODAK KAF-8300) that has a 100% optical fill factor with W~5 μm, and an active area of ~5 $mm^2$. For W~5 μm, to reach a resolution of ~500 nm without using any lenses over an FOV of ~5 $mm^2$, a specially designed array of sub-wavelength apertures 64 that are positioned directly above the active region of the CCD chip can be used.

Image Recovery Process

To explore the details of the digital image recovery process, assume that the sensor array has $M_1 \times M_2$ pixels, and that each pixel has $N_1 \times N_2$ sub-wavelength apertures on it. In this case, this embodiment captures $N_1 \times N_2$ frames of the sensor array for $N_1 \times N_2$ different illumination conditions. If each acquired frame as $I(a,b,c,d)$, where a and b denote the pixel number within the sensor array; and c and d denote the aperture number within each pixel that was on resonance for the acquisition $I(a,b,c,d)$. Therefore, one can write: $a=[1:M_1]$, $b=[1:M_2]$, $c=[1:N_1]$ and $d=[1:N_2]$. One can digitally compute the final high resolution image ($I_{MONA}$) (MONA is an acronym for Microscopy with On-Chip Nano-Apertures) by reordering the measured data, $I(a,b,c,d)$, as: $I_{MONA}((a-1) \cdot N_1+c; (b-1) \cdot N_2+d)=I(a,b,c,d)$. Notice that even though each frame of the sensor array has only $M_1 \times M_2$ pixels, the final high resolution image of this embodiment has $N_2 \cdot M_1 \times N_2 \cdot M_2$ over an FOV that is identical to the active area of the sensor array. Therefore, the resolution of the final high resolution image is improved by a factor of $N_1$ and $N_2$ times, along x and y, with respect to the pixel width at the sensor array. Computationally, the digital recovery process involved in $I_{MONA}$ is not time consuming since it merely involves shifting of the acquired frames.

Transmission Properties of Different Sub-Wavelength Apertures

For the design of the chip 60, the choice of the aperture geometry is needed. The transmission spectrum of a rectangular aperture on a metallic thin film can be computed as shown in FIG. 10, where an x polarized plane wave has been assumed for the illumination of the aperture. The results indicate that the transmission spectrum of a rectangular aperture becomes much narrower and sharper as the aspect ratio, $R=a_y/a_x$ increases, where $a_y$ and $a_x$ define the lengths of the sides of the rectangular aperture. The resonant $\lambda$ in each case is given by $\lambda_c \approx 2a_y$. This indicates that by changing the length of a thin rectangular aperture, where R>>1, one can tune the sharp resonance of the transmission spectrum. Another useful feature of the rectangular geometry is that the transmission coefficient of the orthogonal polarization (along y) is extremely poor.

The above discussed transmission features of a rectangular aperture are quite useful for designing a dense array of sub-wavelength apertures 64, and therefore rectangular aperture is an important candidate to be used in the design of the chip 60. Another promising geometry is a C-aperture geometry, which provides quite high light-throughput within a compact space. The compact design of a C-aperture can especially be very useful for designing resonant apertures at the longer wavelengths of the scanning range to satisfy the space requirement (i.e., $A^2$) of each aperture. The resonance wavelength can easily be tuned by varying the dimensions of $H_t$, $H_b$, $W_a$, and $W_b$ as seen in FIG. 11. This design flexibility of the C-aperture, together with its high transmission efficiency and compact design makes it a perfect candidate to be used in the design of the aperture array in this embodiment. Some other promising aperture geometries that can be used in the design of the chip 60 include circular apertures, elliptical apertures, annular apertures, bowtie apertures, square coaxial apertures, etc.

Research Design and Methods

The lensfree on chip imaging platform using an array of apertures achieves a high spatial resolution of ~500 nm over a field-of-view (FOV) of >5 mm² and with an imaging speed of >150 mm²/min. In this imaging modality, a planar array of sub-wavelength metallic apertures are fabricated on an optoelectronic chip, such that each period of the array will have uniquely different apertures, each of which is resonant at a distinct illumination wavelength and polarization combination. The same period of apertures will then be identically repeated in space to cover the entire FOV (i.e., the active area) of the opto-electronic sensor chip. The illumination wavelength and polarization will be scanned as a function of time, and multiple low resolution transmission images of the object will be acquired at the sensor array, one for each illumination condition. By digitally combining these low resolution widefield images, a much higher resolution image of the entire FOV of the sensor array will be rapidly recovered.

Design of the Array

The design of the array of apertures 64 is one an important aspect of this embodiment. Each period of the array will have a unique design of $N_1 \times N_2$ structures that are densely packed together. All of these nano-structures of one period of the chip have to be designed to have different shapes, sizes and orientations in order to be on resonant at a different $(\lambda, p)_n$. This nano-array within one period will then be repeated identically over the entire FOV of the low NA microscope. Therefore, the design complexity in this embodiment does not increase with the FOV. The fabrication time of the chip 60, however, will be linearly scaled to the area of the FOV.

By utilizing two orthogonal polarizations, one can use the same geometry twice, i.e., at the same illumination wavelength, two nano-structures of the same geometry and size can be used within a period. While apertures 64 have been primarily discussed in the context of this embodiment, it should be understood that antennae may be substituted in their place. However, these two structures will have a 90° rotation with respect to each other to be resonant on e.g., linear orthogonal polarizations. Thus, the total number of unique aperture/antenna geometries that needs to be designed in the chip 60 is $K=N_1 \times N_2/2$. These aperture/antenna geometries will be labeled with their center wavelengths that they are resonant at, i.e., $\lambda_1, \lambda_2 \ldots, \lambda_K$ and $\lambda_1^*, \lambda_2^* \ldots, \lambda_K^*$ where '*' denotes the same nano-structure rotated by 90°, corresponding to the orthogonal polarization state as seen in FIG. 12.

To achieve a resolution enhancement of $N_1$ and $N_2$ times along each direction (x and y), the nano-structures have to function individually, i.e., there should be minimum coupling among the neighboring apertures/antennas. Therefore, at the resonant illumination condition for one particular aperture/antenna geometry and orientation, the remaining nano-structures within the same period should all transmit/emit very poorly. To guarantee this behavior over the entire FOV of the chip, this may be confirmed by:

(1) extensive study using Finite Difference Time Domain (FDTD) simulations for designing proper aperture/antenna geometries, orientations and sizes that do not couple to each other;

(2) Physically separate the nano-structures that are resonant at neighboring wavelengths ($\lambda_n$ and $\lambda_{n+1}$), i.e., there will be a deterministic, but non-sequential hopping of the resonant spot within each period as a function of the illumination wavelength; and (3) Change the resonance polarization condition by e.g., 90° for adjacent nano-structures.

One example of a computer assisted design of the distribution of the apertures within one pixel is given in FIG. 12 for $N_1=N_2=10$. The design criterion for the distribution of the sub-wavelength apertures in FIG. 12 is that every aperture's resonance condition is at least three (3) resonant wavelengths away from it nearest twenty-four (24) neighboring apertures. This implies that for all the twenty five (25) apertures that fall within any 5A×5A area of the pixel (e.g., 2.5 µm×2.5 µm), the resonance $\lambda$ of each aperture will be quite away from the others. Moreover, the polarization condition within the same area is always switched between two orthogonal polarizations for the neighboring apertures. These two properties make the design of the chip quite powerful by minimizing the crosstalk among the apertures. An alternative distribution of the apertures could easily be implemented by changing the design criterion to provide more isolation among different apertures within a pixel. For this purpose, FDTD simulations may be used to design appropriate geometries/orientations for the aperture array, and to numerically test its near-field and far-field transmission properties as a function of $(\lambda, p)_n$.

Calibration and Testing of the Chip

Calibration and testing of the fabricated chip 60 is needed to avoid artifacts in the final high resolution image 72. In this embodiment, there exists a total of $N_1 \times N_2$ apertures 64 within each pixel of the image sensor 66. However, all of these apertures 64 exhibit different transmission coefficients at their designed resonance conditions. In addition, the fabrication process of these apertures will introduce variations in the transmission coefficient of the same aperture geometry located at different pixels. Furthermore, the QE of the active region of the sensor will vary depending on $\lambda$. Therefore, there is a need to calibrate a given chip 60 to take into account such effects. This calibration process can be achieved by acquiring a MONA image ($M_0$) without any object being present on the chip 60. $M_0$ will yield a non-uniform intensity pattern due to the above mentioned variations in the system. However, it also provides an exact map of the desired calibration coefficients. For any object that is positioned on the MONA chip 60, one can simply calibrate the final image by dividing the computed MONA image by $M_0$. This way, artifacts in the final image that would normally result due to variations in e.g., the transmission efficiency of each aperture 64 can be eliminated. The thin oxide layer 63 on the aperture plane ensures that $M_0$ of a given MONA chip 60 will remain the same for any object of interest.

Following the fabrication steps outlined earlier, an array of apertures 64 can be fabricated onto the active region of the image sensor 66, where each aperture 64 will be uniquely brought to resonance at a desired illumination condition. A collimated tunable beam 62 will illuminate the object of interest from behind, and the transmitted light distribution will be sampled by the resonant apertures without any lenses. To avoid blooming at each acquired CCD frame, the illumination power can be dynamically modified using a feedback control that rejects a frame if the well depth of any pixel of the CCD is reached. This ensures that there is no saturation/blooming in any of the acquired frames during the wavelength scanning procedure. After all the frames corresponding to one polarization state are acquired, the linear polarization of the tunable beam will be rotated by 90°, and the wavelength scanning of the light source 62 will start again. All these acquired images will be processed as discussed above to yield $I_{MONA}$. The final high resolution MONA image of the object will be obtained after calibration of the acquired data i.e., $I_{MONA}/M_0$.

Spatial Resolution Issues

In the MONA embodiment, the spatial resolution depends on three quantities: (1) the distance (S) between the object surface and the aperture plane of the sensor chip 60; (2) the physical spacing (A) between two neighboring apertures 64; and (3) the effective modal width of a resonant aperture 64. The last two factors on resolution are related to each other: for proper operation, the effective width of a resonant aperture has to be designed to be smaller than the distance between two apertures 64 (i.e., each aperture will act independent from the others). Therefore, for a properly designed chip 60, the final spatial resolution should only depend on S and A.

By using the current state of nano-fabrication tools (e.g., electron beam lithography), one can achieve A~500 nm, which implies that each one of the apertures 64 in a given pixel will have to fit into an area of $A^2$~500 nm×500 nm. For a pixel size of W, this implies that $\sim(W/A)^2$ different apertures 64 need to be fabricated within each pixel of the sensor array. Choosing a larger A would make the design of the aperture array an easier task, at the cost of reduced resolution. Meanwhile, a smaller A value would be more difficult to achieve since the cross-talk among different apertures would be harder to minimize.

Figure 13A:
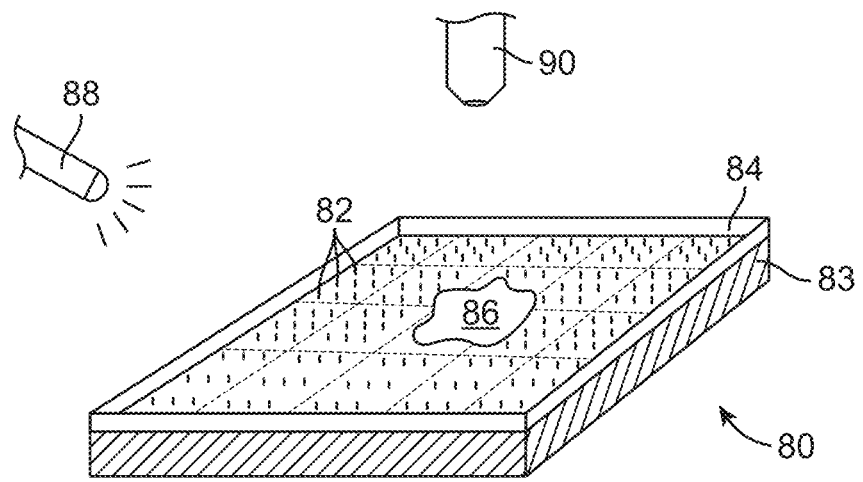
FIG. 13A illustrates a device according to one embodiment that uses sub-wavelength antennas on a glass substrate. A regular darkfield reflection microscope is illustrated which can be used for both illumination and collection.
Figure 13B:
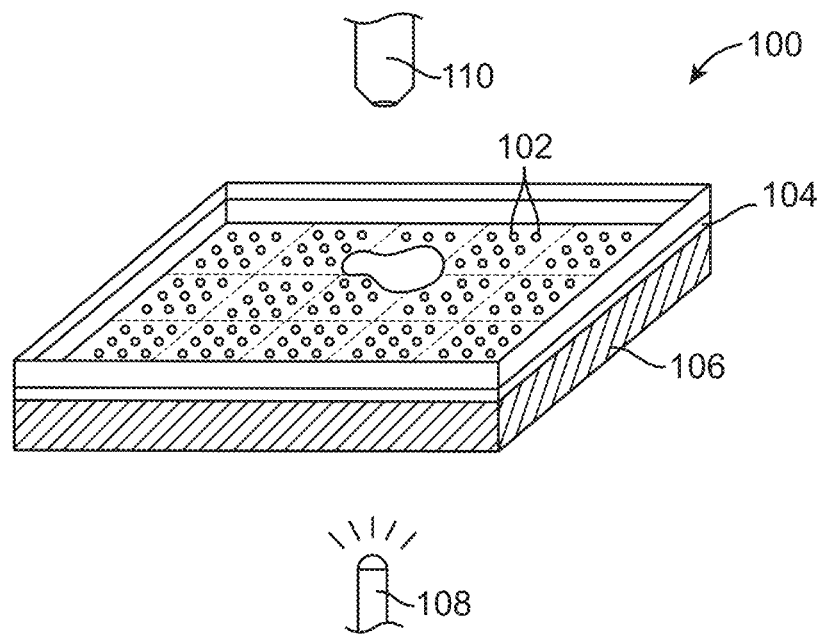
FIG. 13B illustrates a device according to another embodiment that uses sub-wavelength apertures formed in a metal film. The device is used in transmission mode.

FIGS. 13A and 13B illustrate another embodiment of the invention that, similar to the MONA embodiment, is utilizes a tunable light source in conjunction with a chip 80 that includes a nano-patterned surface that may include arrays of apertures or antennas in conjunction with a conventional low NA microscope. In this embodiment, there is no image sensor used in conjunction with the chip 80. Rather, the microscopic modality in this embodiment converts a low NA imaging system, running either in transmission or reflection mode, into a high resolution microscope with a large FOV. The limiting effects of the low NA of the system on resolution is removed by using the period arrays of sub-wavelength structures (i.e., apertures or antennas) that are resonant at specific wavelength/polarization combinations. In this embodiment, the object to be imaged (e.g., cells) are positioned directly onto a specially designed sensor chip 80; and the illumination of the object is achieved by using a tunable light source 88, i.e., the wavelength and polarization is scanned as a function of time.

FIG. 13A illustrates an embodiment of a chip 80 that is used in a reflection geometry. Here, the chip 80 includes an array of antennas 82 on the surface of the chip. The antennas 82 may be formed on a substrate 83 such as glass. The antennas 82 can have any number of configurations including rod or post-like structures. For example, the antennas 82 can include metallic rods. The behavior of the rod may be altered by the materials used in the rod or the geometry of the same (e.g., aspect ratio). The antennas 82 are coated with a thin layer of substantially optically transparent material 84 (e.g., oxide coating). For example, this may be a thin, transparent oxide layer of ~50-100 nm thick $SiO_x$. The major function of this layer is to preserve the designed resonance properties of each antenna/aperture, i.e., object induced changes to the resonance behavior are minimized. A sample or object 86 can be placed directly on top of the oxide layer 84. A tunable light source 88 (wavelength and polarization) directs illumination onto the object 86. A low NA microscope 90 (or microscope objective) is captures reflected illumination.

FIG. 13B illustrates an embodiment of a chip 100 used in a transmission geometry. Here, the chip 100 includes an array of apertures 102 formed in a metal layer 104 that is deposited on an optically transparent substrate 106. The metal layer 104 is deposited on, for example, a glass substrate 106. The metal layer may include ~100-150 nm thick Al which is deposited onto the glass substrate 106 using electron beam or thermal evaporation. Following evaporation, apertures 102 are formed therein using electron beam lithography, FIB, or even soft lithography techniques disclosed herein. It should be noted that the antennas 82 referred to in FIG. 13A are formed in a similar manner with the difference being that for antennas 82, the lithography steps are modified, i.e., the initial metal evaporation can be eliminated. After the full transfer of the antenna pattern onto a resist film, a metal evaporation step followed by a standard lift-off procedure could be used to define the metallic antenna-array on a glass substrate 106. Like the prior embodiment, apertures 106 are coated with a thin layer of substantially optically transparent material 107 (e.g., oxide coating). For example, this may be a thin, transparent oxide layer of ~50-100 nm thick $SiO_x$.

Still referring to FIG. 13B, in this embodiment, the tunable light source 108 is located on an opposite side of the chip 100 as the low NA microscope 110 (or microscope objective) is captures reflected illumination. Tuned light is thus emitted from the tunable light source 108 and passes through the apertures 102, through the object, and then is received by the low NA microscope 110.

The top view of the array configuration of the embodiment of FIG. 13A would look the same as the configuration of FIG. 9C. Every resolution unit of the low NA microscope (i.e., $\sim W^2$) has $N_1 \times N_2$ distinct antennas 82, each of which has a different resonance condition at a unique wavelength and polarization combination $(\lambda, p)_n$. The same sub-wavelength array (dashed 4×4 area) is repeated over the entire FOV of the microscope. The object to be imaged is directly positioned onto the oxide layer 84. The limiting effect of the low NA of the microscope on resolution is removed by scanning the wavelength and polarization of the tunable light source 88. Typical values of W and A are 2.5 and 0.5 μm, respectively, i.e., $N_1=N_2=5$.

By changing $(\lambda, p)_n$, one can effectively scan the entire area of the chip 80, 100, with a scanning step size that equals to the distance between two neighboring nano-structures, i.e., A in FIG. 9C. Assuming an array of $N_1 \times N_2$ sub-wavelength structures per each period, this method requires capturing of $N_1 \times N_2$ different images from the low NA microscope 90, 110, each of which corresponds to a different $(\lambda, p)_n$. Thus, by combining these low resolution images, one can improve the resolution to be $N_1$ and $N_2$ times better than the resolution of the low NA system along each direction (x and y). An image recovery method like the image recovery method described above with respect to the MONA embodiment is used to recover images. That is, digital images of either the reflected or transmitted light may be captured by an image sensor like that disclosed herein. These digitally captured images can then be used as the basis for image reconstruction.

While embodiments have been shown and described, various modifications may be made without departing from the scope of the inventive concepts disclosed herein. For example, while several embodiments have been described herein it should be appreciated that various aspects or elements are interchangeable with other separately embodiments. The invention(s), therefore, should not be limited, except to the following claims, and their equivalents.

What is claimed is:

1. A lensfree imaging and sensing device for imaging a temporary or permanently stationary object within a sample comprising:

an image sensor comprising an array of pixels;
a substantially optically transparent layer disposed above the image sensor;
a substantially optically opaque layer disposed above the substantially optically transparent layer, the substantially optically opaque layer comprising a plurality of apertures extending through the substantially optically opaque layer, wherein a plurality of separate apertures overlie a single pixel of the sensor array and wherein each of the plurality of separate apertures overlying a single pixel of the sensor array exhibits a resonant transmission predominantly at a single wavelength and polarization combination, $(\lambda,p)_n$;
an illumination source configured to illuminate the sample, wherein an optical path defined between the object and the image sensor is free of any optical lenses; and
at least one processor operatively coupled to the image sensor.

2. The device of claim 1, wherein the substantially optically opaque layer comprises a metallic layer comprising a plurality of apertures extending through the metallic layer and configured to receive a sample thereon.

3. The device of claim 1, further comprising an intervening layer between the sample and the substantially optically opaque layer.

4. The device of claim 3, wherein the intervening layer comprises an oxide.

5. The device of claim 1, wherein the substantially optically opaque layer is functionalized with one or more molecules.

6. The device of claim 1, wherein the plurality of apertures are dimensioned smaller than the wavelength of light from the illumination source.

7. The device of claim 1, further comprising a polarizer interposed between the illumination source and the sample.

8. The device of claim 1, wherein the at least one processor is configured to reconstruct a transmission pattern at or near the substantially optically opaque layer based on a plurality of transmission patterns obtained by the image sensor.

9. The device of claim 1, wherein the at least one processor is configured to output a two dimensional cross correlation coefficient comparing transmission patterns of a plurality of transmission patterns obtained by the image sensor.

10. A system for imaging temporary or permanently stationary objects within a sample comprising:
an image sensor comprising an array of individual pixels;
a substantially optically opaque layer disposed above the sensor array, the substantially optically opaque layer comprising an array of apertures extending there through, wherein a plurality of separate apertures overlie a single pixel of the sensor array and wherein each of the plurality of separate apertures overlying a single pixel of the sensor array exhibits a resonant transmission predominantly at a single wavelength and polarization combination, $(\lambda,p)_n$;
a substantially optically transparent layer disposed over the substantially optically opaque layer, the substantially optically transparent layer configured to receive the sample thereon;
a tunable illumination source configured to illuminate the sample and cast one or more shadows on the image sensor, the illumination source being tunable with respect to illumination wavelength and polarization; and
at least one processor configured to receive a plurality of lower resolution image frames from the sensor array at a plurality of tuned wavelengths and polarizations, wherein the at least one processor is further configured to output a high resolution image based in part on the plurality of lower resolution images.

11. The system of claim 10, wherein the substantially optically opaque layer comprises a metallic layer.

12. The system of claim 10, wherein the substantially optically transparent layer comprises an oxide layer.

13. The system of claim 10, wherein each of the separate apertures overlying a single pixel of the sensor array vary with respect to one or more of shape, size, and orientation.

* * * * *